(12) United States Patent
Haegel et al.

(10) Patent No.: US 9,139,652 B2
(45) Date of Patent: Sep. 22, 2015

(54) METHOD FOR INCREASING M1 MACROPHAGES IN A PATIENT

(71) Applicant: TRANSGENE SA, Illkrich (FR)

(72) Inventors: Hélène Haegel, Illkirch (FR); Rêmy Hallet, Strasbourg (FR)

(73) Assignee: Transgene SA, Illkirch (FR)

( * ) Notice: Subject to any disclaimer, the term of this patent is extended or adjusted under 35 U.S.C. 154(b) by 0 days.

(21) Appl. No.: 14/352,262

(22) PCT Filed: Oct. 19, 2012

(86) PCT No.: PCT/EP2012/070805
§ 371 (c)(1),
(2) Date: Apr. 16, 2014

(87) PCT Pub. No.: WO2013/057281
PCT Pub. Date: Apr. 25, 2013

(65) Prior Publication Data
US 2014/0255417 A1    Sep. 11, 2014

(30) Foreign Application Priority Data

Oct. 21, 2011   (EP) .................................. 11306368

(51) Int. Cl.
*C07K 16/28*   (2006.01)

(52) U.S. Cl.
CPC ......... *C07K 16/2866* (2013.01); *C07K 2317/34* (2013.01); *C07K 2317/54* (2013.01); *C07K 2317/73* (2013.01); *C07K 2317/76* (2013.01)

(58) Field of Classification Search
CPC ........... C07K 16/2866; C07K 2317/34; C07K 2317/54; C07K 2317/73; C07K 2317/76
See application file for complete search history.

(56) References Cited

U.S. PATENT DOCUMENTS

2011/0178278 A1    7/2011   Haegel et al.

OTHER PUBLICATIONS

Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
S. Gordon, "Alternative Activation of Macrophages," *Nature Reviews*, Immunology, 3: 23-35 (2003).
E.Y. Lin et al., "Colony-stimulating Factor 1 Promotes Progression of Mammary Tumors to Malignancy," *J. Exp. Med.*, 193(6): 727-739 (2001).
C.J. Sherr et al., "Inhibition of Colony-Stimulating Factor-1 Activity by Monoclonal Antibodies to the Human CSF-1 Receptor," *Blood*, 73(7): 1786-1793 (1989).
A. Sica et al., "Tumour-associated macrophages are a distinct M2 polarised population promoting tumour progression: Potential targets of anti-cancer therapy," *Eur. J. Cancer*, 42: 717-727 (2006).
F.A.W. Verreck et al., "Human IL-23-producing type 1 macrophages promote but IL-10-producing type 2 machrophages subvert immunity to (myco)bacteria," *PNAS*. 101(13): 4560-4565 (2004).
International Search Report and Written Opinion mailed Apr. 24, 2013, for International Patent Application No. PCT/EP2012/070805, filed Oct. 19, 2012 (14 pages).
Genecards. (CSR-1R) [retrieved on Oct. 2-14, 2013], citation may be viewed at <URL: http://web.archive.org/web/20110827020850/http://www/genecards.org/cgi-bin/carddisp.pl?gene=CSF1R> published on Aug. 27, 2011 as per Wayback Engine.
US 8,900,581, 12/2014, Dimoudis et al. (withdrawn)*

* cited by examiner

*Primary Examiner* — Robert Landsman
(74) *Attorney, Agent, or Firm* — Finnegan, Henderson, Farabow, Garrett & Dunner, L.L.P.

(57) ABSTRACT

The invention is generally directed to promoting M1-type (macrophage M1 polarization) immune response by administering a compound that modulates macrophage activation. The invention is directed to the use of an antibody able to bind to CSF-IR for modulating macrophage activation. The invention is also directed to methods for evaluating the dose efficacy of an antibody able to bind to CSF-IR in a patient by assessing the in vivo or in vitro activation of macrophages. The invention is further directed to post-treatment companion test and assays to assess the effect of an antibody able to bind to CSF-IR on a subject being treated.

14 Claims, 8 Drawing Sheets

METHOD FOR INCREASING M1 MACROPHAGES IN A PATIENT

Figure 1:
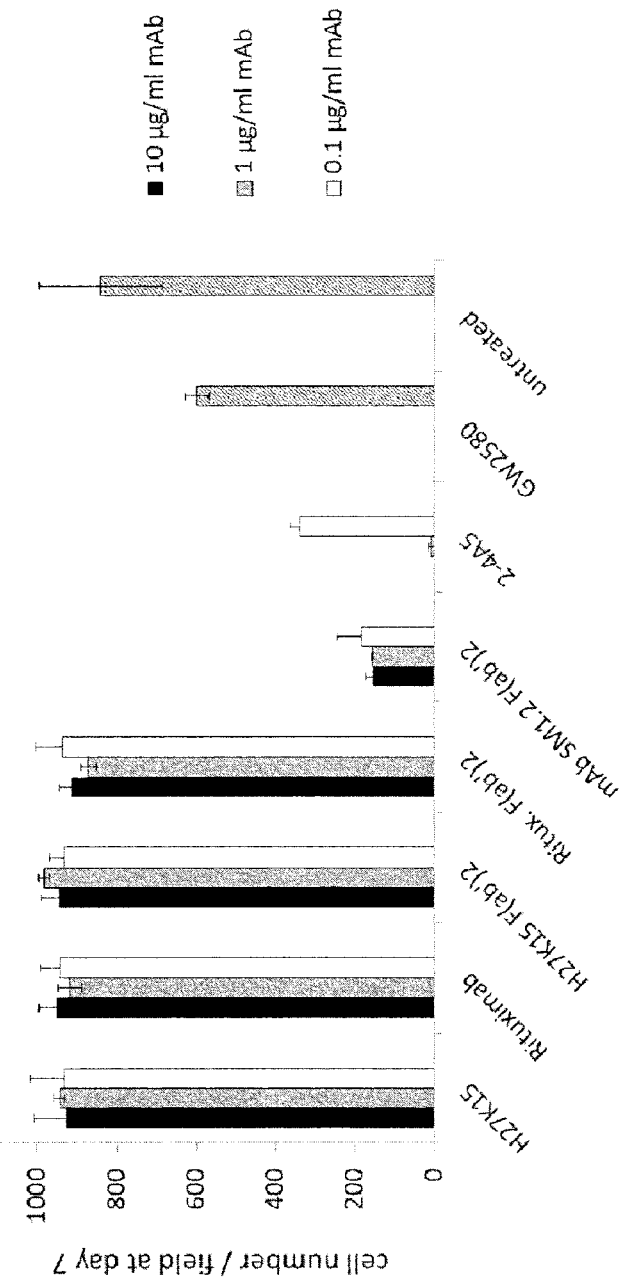

This application is the United States national stage of PCT/EP2012/070805, filed Oct. 19, 2012, (published as WO 2013/057281), which claims priority to European Patent Application No. 11 306 368.9, filed Oct. 21, 2011, all of which are incorporated herein by reference.

SUMMARY OF THE INVENTION

The invention is generally directed to promoting M1-type (macrophage M1 polarization) immune response by administering a compound that modulates macrophage activation, also called macrophage polarization. The invention is directed to the use of an antibody able to bind to CSF-1R for modulating macrophage activation/polarization. The invention is also directed to methods for evaluating the dose efficacy of an antibody able to bind to CSF-1R in a patient by assessing the in vivo or in vitro polarization of macrophages. The invention is further directed to post-treatment companion test and assays to assess the effect of an antibody able to bind to CSF-1R on a subject being treated.

During inflammation, circulating monocytes are recruited to the site of inflammation where they adopt a macrophage phenotype dictated by the presence of specific cytokines and growth factors. Mature macrophages are divided into two populations, M1-polarized or "classically activated" and M2-polarized or "alternatively activated." Macrophages are important tumor-infiltrating cells and play pivotal roles in tumor growth and metastasis. In most solid tumors, the existence of macrophages is advantageous for tumor growth and metastasis. Recent studies indicate that tumor-associated macrophages (TAMs) show a M2 phenotype. These tumor-associated macrophages (TAM) produce interleukin IL-10 and transforming growth factor (TGF) β to suppress general antitumor immune responses. Meanwhile, TAMs promote tumor neo-angiogenesis by the secretion of pro-angiogenic factors and define the invasive microenvironment to facilitate tumor metastasis and dissemination. For these reasons, selective depletion of M2 TAMs has been considered as a novel approach to anti-cancer therapy (Sica et al., 2006, European Journal of Cancer, 42,717-727).

Macrophages participate in immune responses to tumors in a polarized manner. The M1 differentiation is triggered by GM-CSF and further stimulated by interferon-γ (IFN-γ), bacterial lipopolysaccharide (LPS), or tumor necrosis factor α (TNFα), and is mediated by several signal transduction pathways involving signal transducer and activator of transcription (STAT), nuclear factor kappa-light-chain-enhancer of activated B cells (NFκB), and mitogen-activated protein kinases (MAPK). These events enhance the production of agents such as the reactive oxygen species and nitric oxide (NO) and promote the subsequent inflammatory immune responses by increasing antigen presentation capacity and inducing the Th1 immunity through the production of cytokines such as IL12. In contrast, M2 macrophage activation is used to describe macrophages activated in ways other than the M1 activation including IL4/IL13-stimulated macrophages, IL10-induced macrophages and immune complex-triggered macrophages. Among many molecular differences between M1 versus M2 activation, the ratio of IL12 and IL10 production is critical to distinguish M1 and M2 macrophages. Noticeably, TAMs share many properties of M2 macrophages.

TAMs exhibit a M2 profile characterized not only by a IL-12$^{low}$IL-10$^{high}$ phenotype but also high FcR-mediated phagocytic capacity associated with regulatory functions (Schmieder et al. 2012, Semin Cancer Biol., 22, 289-297). The haemoglobin scavenger receptor (CD163) has been identified as a marker of M2-polarized macrophages which is expressed by TAMs (Ambarus et al. 2012, 375,196-206). TAMs can represent the most abundant immunosuppressive cell population in the tumor microenvironment, recruited by CSF-1 and CCL-2 (MCP-1) (Sica et al. 2006, Eur J. Cancer., 42, 717-727).

Similarly, the alternatively activated M2 macrophages have been implicated in several pathologies, the most prominent of which are allergy and asthma (Duffield, 2003, Clin. Sci. 104, 27; Gordon, 2003, Nat. Rev. Immunol., 3, 23; Dagupta and Keegan, J. Innate Immun., 2012, 4, 478).

The Inventors have now shown that certain monoclonal antibodies are able to switch M2 macrophages towards M1 macrophages (i.e. to induce the differentiation of M1 rather than M2 macrophages). They have shown that the said monoclonal antibodies are able to down regulate surface FcγRI (CD64) and FcγRIII (CD16) to down regulate MCP-1 (Macrophage Chemotactic Protein 1, also called CCL-2), IL-6, MMP9 and/or IL-10 production, and to promote IL-12, IL-10, TNF-α production. They have further shown that the said monoclonal antibodies inhibit the differentiation of CD163$^+$M2-type macrophages from human monocytes and increases M1/M2 macrophage ratios.

DISCLOSURE OF INVENTION

The invention is broadly directed to methods for immunomodulation by modulating macrophage activation.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. The term "about x" further includes x value.

As used herein, "comprising" and "comprise" are intended to indicate that the kits of parts, products, compositions and methods include the referenced components or steps, but not excluding others. For example, "a composition comprising x and y" encompasses any composition that contains x and y, no matter what other components may be present in the composition. Likewise, "a method comprising the step of x" encompasses any method in which x is carried out, whether x is the only step in the method or it is only one of the steps, no matter how many other steps there may be and no matter how simple or complex x is in comparison to them.

"Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

According to a first embodiment, the present invention concerns an immunomodulation method by modulating M2 macrophage activation in a patient suffering from conditions associated with undesirable M2 macrophage polarization, wherein said method comprises the step of administering to the said patient an effective amount of an antibody able to bind to CSF-1R. The invention is more specifically directed to such a method for immunomodulation wherein said patient is further suffering from conditions associated with CSF-1R activity.

According to one special embodiment, the present invention concerns the use of an antibody able to bind to human CSF-1R for modulating M2 macrophage polarization, especially in a patient suffering from conditions associated with undesirable M2 macrophage polarization. According to one special embodiment, said patient is further suffering from conditions associated with CSF-1R activity.

The present application refers to "modulating macrophage polarization/activation". This term means that the modulatory antibodies of the Invention cause a decrease in the M2 macrophage activation pool and/or increase in M1 macrophages pool, preferably a decrease in the M2 macrophage activation pool and an increase in M1 macrophages pool. Thus, the M1/M2 ratio increases. This can be indicated, as disclosed herein, by changes in the levels of factors that are associated with M1 and M2 macrophages. Examples of such factors are membrane markers such as CD64 or CD163, cytokines such as IL6, IL10 or IL12, interferons, MCP-1, MMP9, etc. . . . This "modulating macrophage activation" in patients can be appreciated for example by measuring increase of the IL12/IL10 ratio, MCP-1 or IL-6 level, or the $CD163^-/CD163^+$ macrophage ratio following administration to a patient of an antibody able to bind to CSF-1R of the Invention.

According to another embodiment, the present invention concerns a method for increasing M1 macrophages pool in a patient suffering from conditions associated with undesirable M2 polarization, wherein said method comprises the step of administering to the said patient an effective amount of an antibody able to bind to CSF-1R. The invention is more specifically directed to such a method for immunomodulation wherein said patient is further suffering from conditions associated with CSF-1R activity.

According to special embodiment, said method for increasing M1 macrophages pool in a patient suffering from conditions associated with undesirable M2 polarization, further decreases the macrophage M2 pool.

"Patient" means a vertebrate, such as a mammal, such as a human. Mammals include, but are not limited to humans, dogs, cats, horses, cows, and pigs. According to the present invention, the "patient" is suffering from conditions associated with undesirable M2 activation, and according to particular embodiment is further suffering from conditions associated with CSF-1R activity.

The invention is also more specifically directed to one method for reducing macrophage pro-tumoral functions (i.e. tumorigenicity) and/or increasing macrophage tumor suppression activity in a patient, especially in patient suffering from conditions associated with undesirable M2 polarization and/or from conditions associated with CSF-1R activity, wherein said method comprises the step of administering to the said patient an effective amount of an antibody able to bind to CSF-1R.

According to special embodiment, the method of the invention represses at least one macrophage pro-tumoral functions selected in the group consisting of tumor invasion, metastasis, tumor cell proliferation, tumor growth, tumor survival, neo-angiogenesis, suppression of innate or adaptive immunity and extracellular matrix remodeling.

Thus, with respect to the invention, "modulating macrophage activation/polarization" can further mean that the modulatory antibodies of the Invention reduce at least one macrophage pro-tumoral functions (i.e. tumorigenicity) selected in the group consisting of tumor invasion, metastasis, tumor cell proliferation, tumor growth, tumor survival, neo-angiogenesis, suppression of adaptive or innate immunity and extracellular matrix remodeling.

According to special embodiment, the method of the invention inhibits macrophage MCP-1, MMP-9 and IL-6 production by macrophages, especially human macrophages.

According to special embodiment, the method of the invention down regulates surface FcγRI (CD64) and FcγRIII (CD16) expression on macrophages, especially human macrophages.

According to special embodiment, the method of the invention promotes IL-12 (more particularly IL-12 P70 form) production by macrophages, especially human macrophages and/or upregulates IL-12/IL-10 ratios.

According to special embodiment, the method of the invention modulates the activation state of macrophages by means of secreted factors.

According to special embodiment, the method of the invention reduces at least one of the followings:
 TAM recruitment into tumor;
 at least one macrophage pro-tumoral functions;
 tumor angiogenesis;
 tumor invasion and metastasis;
 tumor growth;
 tumor cell proliferation
in patients, especially in patients suffering from conditions associated with undesirable M2 macrophage polarization. According to special embodiment, the said patient is further suffering from conditions associated with CSF-1R activity.

The invention is also directed to methods for driving macrophages towards a M1-type (macrophage M1 polarization) immune response and/or away from a M2-type (macrophage M2 polarization) immune response in patients, especially in patients suffering from conditions associated with undesirable M2 macrophage polarization or in patient suffering from conditions associated with CSF-1R activity, wherein said method comprises the step of administering to the said patient an effective amount of an antibody able to bind to CSF-1R.

The invention is further directed to methods for driving macrophages towards a Th1 immune response or away from a Th2 immune response in patients, especially in patients suffering from conditions associated with undesirable M2 macrophage polarization or in patient suffering from conditions associated with CSF-1R activity, wherein said method comprises the step of administering to the said patient an effective amount of an antibody able to bind to CSF-1R.

The invention is also directed to the use of an antibody able to bind to CSF-1R for modulating macrophage polarization. The invention is also directed to the use of an antibody able to bind to CSF-1R for driving macrophages towards a M1-type (macrophage M1 polarization) immune response. The invention is also directed to the use of an antibody able to bind to CSF-1R for inducing macrophages to stimulate a Th1-type immune response. The invention is also directed to the use of compositions, such as pharmaceutical compositions, comprising an antibody able to bind CSF-1R for modulating macrophage activation, for driving macrophages towards a M1-type (macrophage M1 polarization) immune response and/or inducing macrophages to stimulate a Th1-type immune response.

As used herein, the term "able to bind to" refers to a binding reaction which is determinative of the presence of a target protein in the presence of a heterogeneous population of proteins and other biologics. Thus, under designated assay conditions, the antibody according to the invention bind preferentially to at least part of the CSF-1R and preferably do not bind in a significant amount to other components present in a test sample. Specific binding between the antibody according to the invention and the CSF-1R target means that the binding affinity is of at least $10^3$ M$^{-1}$, and preferably $10^5$ M$^{-1}$, $10^6$ M$^{-1}$, $10$ M$^{-1}$, $10^8$ M$^{-1}$, $10^9$ M$^{-1}$ or $10^{10}$ M$^{-1}$.

As used herein, the term "CSF-1R" refers to the human CSF1 receptor.

As used herein, "antibody" or "Ab" is used in the broadest sense. Therefore, an "antibody" or "Ab" can be naturally occurring or man-made such as monoclonal antibodies (mAbs) produced by conventional hybridoma technology, recombinant technology and/or a functional fragment thereof. Antibodies of the present invention are preferably monoclonal antibodies (mAb).

As used herein, the term "variable region" refers to the variable region, or domain, of the light chain (VL) or heavy chain (VH) which contains the determinants for binding recognition specificity. The variable domains are involved in antigen recognition and form the antigen binding site. The variable region of both the heavy and light chain is divided into segments comprising four framework sub-regions (FR1, FR2, FR3, and FR4), interrupted by three stretches of hypervariable sequences, or the complementary determining regions (CDR's), as defined in Kabat's database, with the CDR1 positioned between FR1 and FR2, CDR2 between FR2 and FR3, and CDR3 between FR3 and FR4. Without specifying the particular sub-regions as FR1, FR2, FR3 or FR4, a framework region as referred by others, represents the combined FR's within the variable region of a single, naturally occurring immunoglobulin chain. As used herein, a FR represents one of the four sub-regions, and FR's represents two or more of the four sub-regions constituting a framework region. The framework region of an antibody is the combined framework regions of the constituent light and heavy chains and serves to position and align the CDR's. The CDR's are primarily responsible for forming the binding site of an antibody conferring binding specificity and affinity to an epitope of an antigen. Within the variable regions of the H or L chains that provide for the antigen binding regions are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure. The variable heavy and light chains of all antibodies each have 3 CDR regions, each non-contiguous with the others (termed L1, L2, L3, H1, H2, H3) for the respective light (L) and heavy (H) chains.

"Co-administer" means to administer in conjunction with one another, together, coordinately, including simultaneous or sequential administration of two or more agents.

"Effective amount" generally means an amount which provides the desired local or systemic effect, e.g., effective to ameliorate undesirable effects of inflammation, including modulation of activation of macrophages, etc. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art. As used herein, "effective dose" means the same as "effective amount".

According to another embodiment, the present invention relates to the use of an antibody able to bind to human CSF-1R for reducing at least one macrophage pro-tumoral functions selected in the group consisting of tumor invasion, metastasis, tumor growth, tumor survival, neo-angiogenesis, suppression of innate or adaptive immunity and matrix remodeling (i.e. tumorigenicity) and/or increasing macrophage tumor suppression activity in patients, especially patient suffering from conditions associated with undesirable M2 activation, and according to particular embodiment further suffering from conditions associated with CSF-1R activity.

According to another embodiment, the present invention relates to the use of an antibody able to bind to human CSF-1R for inhibiting MCP-1, MMP-9 and IL-6 production by macrophages, especially human macrophages.

According to another embodiment, the present invention relates to the use of an antibody able to bind to human CSF-1R for down regulating surface FcγRI (CD64) and/or FcγRIII (CD16) expression on macrophages, especially human macrophages.

According to another embodiment, the present invention relates to the use of an antibody able to bind to human CSF-1R for promoting IL-12 (more particularly IL-12 P70 form) production by macrophages, especially human macrophages and/or up-regulating the IL-12/IL-10 ratio.

According to another embodiment, the present invention relates to the use of an antibody able to bind to human CSF-1R for modulating the activation state of macrophages by means of secreted factors.

According to another embodiment, the present invention relates to the use of an antibody able to bind to human CSF-1R for reducing TAM recruitment and/or tumor angiogenesis in patients, especially patient suffering from conditions associated with undesirable M2 macrophage polarization, and according to particular embodiment further suffering from conditions associated with CSF-1R activity.

The invention is also more specifically directed to the use of an antibody able to bind to human CSF-1R for reducing TAM recruitment and/or tumor invasion and metastasis in patients, especially patient suffering from conditions associated with undesirable M2 macrophage polarization, and according to particular embodiment further suffering from conditions associated with CSF-1R activity.

The invention is also more specifically directed to the use of an antibody able to bind to human CSF-1R for reducing TAM recruitment and/or tumor growth in patients, especially patient suffering from conditions associated with undesirable M2 macrophage polarization, and according to particular embodiment further suffering from conditions associated with CSF-1R activity.

According to another embodiment, the present invention relates to the use of an antibody able to bind to human CSF-1R for driving macrophages towards a M1-type (macrophage M1 polarization) immune response and/or away from a M2-type (macrophage M2 polarization) immune response in patients, especially patient suffering from conditions associated with undesirable M2 macrophage polarization, and according to particular embodiment further suffering from conditions associated with CSF-1R activity.

According to another embodiment, the present invention relates to the use of an antibody able to bind to human CSF-1R for driving macrophages towards a Th1 immune response and/or away from a Th2 immune response in patients, especially patient suffering from conditions associated with undesirable M2 macrophage polarization, and according to particular embodiment further suffering from conditions associated with CSF-1R activity.

According to preferred embodiments, the said antibody able to bind to human CSF-1R is an antibody that binds to at least one epitope located between position amino acids 20 to 41 of SEQ ID N0:23 (i.e. N-terminal part of the human domain D1). In preferred embodiment, the antibody according to the Invention binds to one epitope located between position amino acids 20 to 39 of SEQ ID N0:23 (i.e. N-terminal part of the human domain D1), to amino acids Asn72, Ser94-Ala95-Ala96, Lys102, Asp131-Pro132-Val133 and Trp159 of SEQ ID N0:23.

In another embodiment, the antibody according to the Invention binds to one epitope located between position amino acids 20 to 41 of SEQ ID N0:23 (i.e. N-terminal part of the human domain D1) and does not bind to any epitope located between position amino acids 42 to 90, and/or between position amino acids 91 to 104, and/or between position amino acids 105 to 199, and/or between position amino acids 200 to 298 of SEQ ID N0:23. According to preferred embodiment, the antibody of the present Invention is able to recognize the minimal epitope located between position amino acids 20 to 41 of SEQ ID N0:23 (i.e. N-terminal part of the human domain D1), preferably to epitope between position amino acids 20 to 39 of SEQ ID N0:23.

In preferred embodiment, the said antibody able to bind to human CSF-1R is an antibody that does not compete with IL-34 ligand for binding to the CSF-1R receptor. The term "does not compete with IL-34 ligand" as used herein refers to no inhibition of the IL34 ligand to its receptor CSF-1R binding.

In preferred embodiment, the said antibody able to bind to human CSF-1R is an antibody that competes partially with CSF-1 ligand for binding to the CSF-1R receptor. The term "competes partially with CSF-1 ligand" as used herein refers to an inhibition of the CSF-1 ligand to its receptor CSF-1R binding which is less than 100%, preferably less than 50%, and even more preferably less than 20%, and advantageously less than 10%. This partial inhibitor only reduces but does not totally exclude ligand binding, the inhibition is called partial inhibition. In preferred embodiment, the said antibody able to bind to CSF-1R is an antibody that is able to partially prevent binding of CSF1 to its receptor CSF-1R, and is not able to totally inhibit said binding. More particularly, the antibodies according to the Invention are able to decrease the CSF-1 binding to CSF-1R by approximately 5 to 10%.

According to one embodiment, the said antibody able to bind to human CSF-1R is an antibody that comprises:
  (i) at least one CDR wherein said CDR is comprising at least five consecutive amino acids of the sequence starting in position 45 and finishing in position 54 of SEQ ID NO:1, of the sequence starting in position 66 and finishing in position 87 of SEQ ID NO:1 or of the sequence starting in position 117 and finishing in position 126 of SEQ ID NO:1;
or,
  (ii) at least one CDR wherein said CDR is comprising at least five consecutive amino acids of the sequence starting in position 44 and finishing in position 56 of SEQ ID NO:2, of the sequence starting in position 66 and finishing in position 76 of SEQ ID NO:2 or of the sequence starting in position 109 and finishing in position 117 of SEQ ID NO:2.

According to a preferred embodiment, the said antibody able to bind to CSF-1R is an antibody that binds specifically to human CSF-1R, and comprises the following CDRs comprising at least five consecutive amino acids:
  of the sequence starting in position 45 and finishing in position 54 of SEQ ID NO:1,
  of the sequence starting in position 66 and finishing in position 87 of SEQ ID NO:1,
  of the sequence starting in position 117 and finishing in position 126 of SEQ ID NO:1,
  of the sequence starting in position 44 and finishing in position 56 of SEQ ID NO:2,
  of the sequence starting in position 66 and finishing in position 76 of SEQ ID NO:2
  or of the sequence starting in position 109 and finishing in position 117 of SEQ ID NO:2.

According to another embodiment, the said antibody able to bind to CSF-1R is an antibody that binds specifically to human CSF-1R, and comprises at least one CDR selected, independently from one another, in the group of the CDR as set forth in:
  the sequence starting in position 45 and finishing in position 54 of SEQ ID NO:1,
  the sequence starting in position 66 and finishing in position 87 of SEQ ID NO:1,
  the sequence starting in position 117 and finishing in position 126 of SEQ ID NO:1,
  the sequence starting in position 44 and finishing in position 56 of SEQ ID NO:2,
  the sequence starting in position 66 and finishing in position 76 of SEQ ID NO:2 and
  the sequence starting in position 109 and finishing in position 117 of SEQ ID NO:2.

According to another embodiment, the said antibody able to bind to CSF-1R is an antibody that binds specifically to human CSF-1R, and comprises the CDR as set forth in:
  the sequence starting in position 45 and finishing in position 54 of SEQ ID NO:1,
  the sequence starting in position 66 and finishing in position 87 of SEQ ID NO:1,
  the sequence starting in position 117 and finishing in position 126 of SEQ ID NO:1,
  the sequence starting in position 44 and finishing in position 56 of SEQ ID NO:2,
  the sequence starting in position 66 and finishing in position 76 of SEQ ID NO:2 and
  the sequence starting in position 109 and finishing in position 117 of SEQ ID NO:2.

According to another embodiment, the said antibody able to bind to CSF-1R is an antibody that binds specifically to human CSF-1R, and comprises at least one CDR comprising an amino acid sequence as set forth in any one of SEQ ID NOs: 5, 6, 7, 8, 9 or 10.

According to a preferred embodiment, the said antibody able to bind to CSF-1R is an antibody that binds specifically to human CSF-1R, and comprises the CDRs comprising amino acid sequences as set forth in SEQ ID NOs: 5, 6, 7, 8, 9 or 10.

According to another embodiment, the said antibody able to bind to CSF-1R is an antibody that binds specifically to human CSF-1R, and comprises (i) at least one CDR comprising an amino acid sequence as set forth in any one of SEQ ID NOs: 11, 12 or 13; or (ii) at least one CDR comprising an amino acid sequence as set forth in any one of SEQ ID NOs: 14, 15 or 16.

According to another embodiment, the said antibody able to bind to CSF-1R is an antibody that binds specifically to human CSF-1R, and comprises the CDR comprising amino acid sequences as set forth in SEQ ID NOs: 11, 12, 13, 14, 15 or 16.

According to another embodiment, the said antibody able to bind to CSF-1R is an antibody that binds specifically to human CSF-1R, and comprises (i) at least one CDR comprising an amino acid sequence as set forth in any one of SEQ ID NOs: 17, 18 or 19; or (ii) at least one CDR comprising an amino acid sequence as set forth in any one of SEQ ID NOs: 20, 21 or 22.

According to another embodiment, the said antibody able to bind to CSF-1R is an antibody that binds specifically to human CSF-1R, and comprises at least one CDR comprising an amino acid sequence as set forth in any one of SEQ ID NOs: 17, 18, 19, 20, 21 or 22.

According to one preferred embodiment, the said antibody able to bind to CSF-1R is an antibody that binds specifically to human CSF-1R, and comprises the CDR comprising amino acid sequences as set forth in SEQ ID NOs: 17, 18, 19, 20, 21 or 22.

According to another embodiment, the said antibody able to bind to CSF-1R is an antibody that binds specifically to human CSF-1R, and comprises a variable region, wherein said variable region comprises the three CDRs as set forth in SEQ ID NOs: 5, 6, and 7.

According to another embodiment, the said antibody able to bind to CSF-1R is an antibody that binds specifically to human CSF-1R, and comprises a variable region, wherein said variable region comprises the three CDRs as set forth in SEQ ID NOs: 8, 9, and 10.

According to another embodiment, the said antibody able to bind to CSF-1R is an antibody that binds specifically to human CSF-1R, and comprises a variable region, wherein said variable region comprises the three CDRs set forth in SEQ ID NOs: 11, 12, and 13.

According to another embodiment, the said antibody able to bind to CSF-1R is an antibody that binds specifically to human CSF-1R, and comprises a variable region, wherein said variable region comprises the three CDRs as set forth in SEQ ID NOs: 14, 15, and 16.

According to another embodiment, the said antibody able to bind to CSF-1R is an antibody that binds specifically to human CSF-1R, and comprises a variable region, wherein said variable region comprises the three CDRs as set forth in SEQ ID NOs: 17, 18, and 19.

According to another embodiment, the said antibody able to bind to CSF-1R is an antibody that binds specifically to human CSF-1R, and comprises a variable region, wherein said variable region comprises the three CDRs as set forth in SEQ ID NOs: 20, 21, and 22.

According to one preferred embodiment, the said antibody able to bind to CSF-1R is an antibody that binds specifically to human CSF-1R, and comprises a variable region, wherein the variable region comprises an amino acid sequence as set forth in SEQ ID NO:3.

In a more preferred embodiment, the said antibody able to bind to CSF-1R is an antibody that binds specifically to human CSF-1R, and comprises a variable region, wherein the variable region is as set forth in SEQ ID NO:3.

In another preferred embodiment, the said antibody able to bind to CSF-1R is an antibody that binds specifically to human CSF-1R, wherein the variable region comprises an amino acid sequence as set forth in SEQ ID NO:4.

In another more preferred embodiment, the said antibody able to bind to CSF-1R is an antibody that binds specifically to human CSF-1R, and comprises a variable region, wherein the variable region is as set forth in SEQ ID NO:4.

According to a preferred embodiment, the said antibody able to bind to CSF-1R is an antibody that binds specifically to human CSF-1R, and comprises:
 a variable region comprising the three CDRs as set forth in SEQ ID NOs: 5, 6, and 7, and
 a variable region comprising the three CDRs as set forth in SEQ ID NOs: 8, 9, and 10.

According to a preferred embodiment, the said antibody able to bind to CSF-1R is an antibody that binds specifically to human CSF-1R, and comprises:
 a variable region comprising the three CDRs as set forth in SEQ ID NOs: 11, 12, and 13, and
 a variable region comprising the three CDRs as set forth in SEQ ID NOs: 14, 15, and 16.

According to a preferred embodiment, the said antibody able to bind to CSF-1R is an antibody that binds specifically to human CSF-1R, and comprises:
 a variable region comprising the three CDRs as set forth in SEQ ID NOs: 17, 18, and 19, and
 a variable region comprising the three CDRs as set forth in SEQ ID NOs: 20, 21, and 22.

According to a preferred embodiment, the said antibody able to bind to CSF-1R is an antibody that binds specifically to human CSF-1R, and comprises:
 a variable region as set forth in SEQ ID NO:3 and
 a variable region as set forth in SEQ ID NO:4.

According to a preferred embodiment, the said antibody able to bind to CSF-1R is an antibody that binds specifically to human CSF-1R, and comprises:
 (i) a heavy-chain variable region comprising:
  the CDR as set forth in the sequence starting in position 45 and finishing in position 54 of SEQ ID NO:1,
  the CDR as set forth in the sequence starting in position 66 and finishing in position 87 of SEQ ID NO:1 and
  the CDR as set forth in the sequence starting in position 117 and finishing in position 126 of SEQ ID NO:1;
 and
 (ii) a light-chain variable region comprising:
  the CDR as set forth in the sequence starting in position 44 and finishing in position 56 of SEQ ID NO:2,
  the CDR as set forth in the sequence starting in position 66 and finishing in position 76 of SEQ ID NO:2 and
  the CDR as set forth in the sequence starting in position 109 and finishing in position 117 of SEQ ID NO:2.

According to another embodiment, the said antibody able to bind to CSF-1R is an antibody that binds specifically to human CSF-1R, and comprises (1) a heavy-chain variable region comprising the three CDRs as set forth in SEQ ID NOs: 5, 6, and 7, and (ii) a light-chain variable region comprising the three CDRs as set forth in SEQ ID NOs: 8, 9, and 10.

According to another embodiment, the antibody of the Invention binds specifically to CSF-1R and comprises (i) a heavy-chain variable region comprising the three CDRs as set forth in SEQ ID NOs: 11, 12, and 13, and (ii) a light-chain variable region comprising the three CDRs as set forth in SEQ ID NOs: 14, 15, and 16.

According to another embodiment, the said antibody able to bind to CSF-1R is an antibody that binds specifically to human CSF-1R, and comprises (i) a heavy-chain variable region comprising the three CDRs as set forth in SEQ ID NOs: 17, 18, and 19, and (ii) a light-chain variable region comprising the three CDRs as set forth in SEQ ID NOs: 20, 21, and 22.

According to a preferred embodiment, the said antibody able to bind to CSF-1R is an antibody that binds specifically to human CSF-1R, and comprises (i) a heavy-chain variable region as set forth in SEQ ID NO:3 and (ii) a light-chain variable region as set forth in SEQ ID NO:4.

According to another embodiment, the said antibody able to bind to CSF-1R is an antibody that binds specifically to human CSF-1R, comprising:

(a) a first variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 has at least five consecutive amino acids of the sequence starting in position 45 and finishing in position 54 of SEQ ID NO:1;
CDR2 has at least five consecutive amino acids of the sequence starting in position 66 and finishing in position 87 of SEQ ID NO:1; and
CDR3 has at least five consecutive amino acids of the sequence starting in position 117 and finishing in position 126 of SEQ ID NO:1; and
(b) a second variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 has at least five consecutive amino acids of the sequence starting in position 44 and finishing in position 56 of SEQ ID NO:2;
CDR2 has at least five consecutive amino acids of the sequence starting in position 66 and finishing in position 76 of SEQ ID NO:2; and
CDR3 has at least five consecutive amino acids of the sequence starting in position 109 and finishing in position 117 of SEQ ID NO:2.

According to another embodiment, the said antibody able to bind to CSF-1R is an antibody that binds specifically to human CSF-1R, comprising:

(a) a first variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 has an amino acid sequence selected from the group consisting of: SEQ ID NO: 5, 11 and 17;
CDR2 has an amino acid sequence selected from the group consisting of: SEQ ID NO: 6, 12 and 18; and
CDR3 has an amino acid sequence selected from the group consisting of: SEQ ID NO: 7, 13 and 19; and
(b) a second variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;

wherein:
CDR1 has an amino acid sequence selected from the group consisting of: SEQ ID NO: 8, 14 and 20;
CDR2 has an amino acid sequence selected from the group consisting of: SEQ ID NO: 9, 15 and 21; and
CDR3 has an amino acid sequence selected from the group consisting of: SEQ ID NO: 10, 16 and 22.

According to another embodiment, the said antibody able to bind to CSF-1R is an antibody that binds specifically to human CSF-1R, comprising any one of the following (i), (ii) or (iii):

(i)
(a) a first variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 is as set forth in SEQ ID NO: 5;
CDR2 is as set forth in SEQ ID NO: 6; and
CDR3 is as set forth in SEQ ID NO: 7;
and
(b) a second variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 is as set forth in SEQ ID NO: 8;
CDR2 is as set forth in SEQ ID NO: 9; and
CDR3 is as set forth in SEQ ID NO: 10;
or
(ii) (a) a first variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 is as set forth in SEQ ID NO: 11;
CDR2 is as set forth in SEQ ID NO: 12; and
CDR3 is as set forth in SEQ ID NO: 13; and
(b) a second variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 is as set forth in SEQ ID NO: 14;
CDR2 is as set forth in SEQ ID NO: 15; and
CDR3 is as set forth in SEQ ID NO: 16;
or
(iii) (a) a first variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 is as set forth in SEQ ID NO: 17;
CDR2 is as set forth in SEQ ID NO: 18; and
CDR3 is as set forth in SEQ ID NO: 19;
and
(b) a second variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 is as set forth in SEQ ID NO: 20;
CDR2 is as set forth in SEQ ID NO: 21; and
CDR3 is as set forth in SEQ ID NO: 22.

According to another embodiment, the said antibody able to bind to CSF-1R is an antibody that binds specifically to human CSF-1R, comprising:
a first variable region comprising the amino acid sequence of SEQ ID NO: 3; and
a second variable region comprising the amino acid sequence of SEQ ID NO: 4.

According to another embodiment, the said antibody able to bind to CSF-1R is an antibody that binds specifically to human CSF-1R, comprising:
a first variable region comprising the amino acid sequence of SEQ ID NO: 1; and
a second variable region comprising the amino acid sequence of SEQ ID NO: 2.

According to another embodiment, the said antibody able to bind to CSF-1R is an antibody that binds specifically to human CSF-1R, comprising:
an heavy chain selected in the group consisting in SEQ ID NO: 24 and SEQ ID NO: 25, and
a light chain selected in the group consisting in SEQ ID NO: 26, SEQ ID NO: 27 and SEQ ID NO: 28.

According to another embodiment, the said antibody able to bind to CSF-1R is an antibody that binds specifically to human CSF-1R, comprising:
a first variable region selected in the group consisting of SEQ ID NO: 29 and SEQ ID NO: 30; and
a second variable region selected in the group consisting of SEQ ID NO: 31, SEQ ID NO: 32 and SEQ ID NO: 33.

According to one preferred embodiment, the said antibody able to bind to CSF-1R is an antibody that binds specifically to human CSF-1R, comprising (a) an heavy chain consisting in SEQ ID NO: 24, and (b) a light chain consisting in SEQ ID NO: 26.

According to another preferred embodiment, the said antibody able to bind to CSF-1R is an antibody that binds specifically to human CSF-1R, comprising (a) an heavy chain consisting in SEQ ID NO:25, and (b) a light chain consisting in SEQ ID NO: 27.

According to one advantageous embodiment, the said antibody able to bind to CSF-1R is an antibody that binds specifically to human CSF-1R, comprising (a) an heavy chain consisting in SEQ ID NO:24, and (b) a light chain consisting in SEQ ID NO:28. Example of the said monoclonal antibody is monoclonal antibody H27K15.

According to one preferred embodiment, the said antibody able to bind to CSF-1R is an antibody that binds specifically to human CSF-1R, comprising (a) first variable region consisting in SEQ ID NO: 29, and (b) a second variable region consisting in SEQ ID NO: 31.

According to another preferred embodiment, the said antibody able to bind to CSF-1R is an antibody that binds specifically to human CSF-1R, comprising (a) first variable region consisting in SEQ ID NO: 30, and (b) a second variable region consisting in SEQ ID NO: 32.

According to one advantageous embodiment, the said antibody able to bind to CSF-1R is an antibody that binds specifically to human CSF-1R, comprising (a) first variable region consisting in SEQ ID NO: 29, and (b) a second variable region consisting in SEQ ID NO: 33. Example of the said monoclonal antibody is monoclonal antibody H27K15.

The antibody, more specifically the human antibody, according to the invention may be of different isotypes, such as IgG, IgA, IgM or IgE. In a preferred embodiment the antibody, more specifically the human antibody, according to the invention is an IgG.

The antibody according to the invention may be glycosylated or non-glycosylated.

As used herein, the term "glycosylation" refers to the presence of carbohydrate units that are covalently attached to the antibody.

The methods of the invention are useful in treatment of conditions associated with undesirable M2 activation and associated with CSF-1R. The methods of the invention are useful in treatment of disease involving inflammation and associated with CSF-1R.

"Patients suffering from conditions associated with undesirable M2 macrophage polarization according to the Invention designate cancer, especially metastatic cancer, progressive fibrotic diseases such as for example idiopathic pulmonary fibrosis (IPF), hepatic fibrosis or systemic sclerosis (Wynn and Barron, 2010, Semin. Liver Dis., 30, 245), allergy and asthma, atherosclerosis and Altzheimer's disease.

According to another embodiment, the present invention relates to methods for driving macrophages towards a M1-type (macrophage M1 polarization)-driven immune response and away from a M2-type (macrophage M2 polarization)-driven immune response in patients suffering from cancer.

According to another embodiment, the present invention relates to methods for driving macrophages towards a M1-type (macrophage M1 polarization) immune response and away from a M2-type (macrophage M2 polarization)-driven immune response in patients suffering from progressive fibrotic diseases.

According to another embodiment, the present invention relates to methods for driving macrophages towards a M1-type (macrophage M1 polarization)-driven immune response and away from a M2-type (macrophage M2 polarization)-driven immune response in patients suffering from allergy.

According to another embodiment, the present invention relates to methods for driving macrophages towards a M1-type (macrophage M1 polarization) immune response and away from a M2-type (macrophage M2 polarization) immune response in patients suffering from asthma.

As used herein, the term "cancer" refers but is not limited to adenocarcinoma, acinic cell adenocarcinoma, adrenal cortical carcinomas, alveoli cell carcinoma, anaplastic carcinoma, basaloid carcinoma, basal cell carcinoma, bronchiolar carcinoma, bronchogenic carcinoma, renaladinol carcinoma, embryonal carcinoma, anometroid carcinoma, fibrolamolar liver cell carcinoma, follicular carcinomas, giant cell carcinomas, hepatocellular carcinoma, intraepidermal carcinoma, intraepithelial carcinoma, leptomanigio carcinoma, medullary carcinoma, melanotic carcinoma, menigual carcinoma, mesometonephric carcinoma, oat cell carcinoma, squamal cell carcinoma, sweat gland carcinoma, transitional cell carcinoma, tubular cell carcinoma, amelioblastic sarcoma, angiolithic sarcoma, botryoid sarcoma, endometrial stroma sarcoma, ewing sarcoma, fascicular sarcoma, giant cell sarcoma, granulositic sarcoma, immunoblastic sarcoma, juxaccordial osteogenic sarcoma, coppices sarcoma, leukocytic sarcoma (leukemia), lymphatic sarcoma (lympho sarcoma), medullary sarcoma, myeloid sarcoma (granulocitic sarcoma), austiogenci sarcoma, periosteal sarcoma, reticulum cell sarcoma (histiocytic lymphoma), round cell sarcoma, spindle cell sarcoma, synovial sarcoma, telangiectatic audiogenic sarcoma, Burkitt's lymphoma, NPDL, NML, NH and diffuse lymphomas. According to a preferred embodiment, the method according to the invention is directed to the treatment of metastatic cancer to bone, wherein the metastatic cancer is breast, lung, renal, multiple myeloma, thyroid, prostate, adenocarcinoma, blood cell malignancies, including leukemia and lymphoma; head and neck cancers; gastrointestinal cancers, including esophageal cancer, stomach cancer, colon cancer, intestinal cancer, colorectal cancer, rectal cancer, pancreatic cancer, liver cancer, cancer of the bile duct or gall bladder; malignancies of the female genital tract, including ovarian carcinoma, uterine endometrial cancers, vaginal cancer, and cervical cancer; bladder cancer; brain cancer, including neuroblastoma; sarcoma, osteosarcoma; and skin cancer, including malignant melanoma or squamous cell cancer.

The present invention further concerns a method for improving the treatment of a cancer patient which is undergoing chemotherapeutic treatment with a cancer therapeutic agent, which comprises co-treatment of said patient along with a method as above disclosed.

The present invention further concerns a method for improving the treatment of a cancer patient which is undergoing immunotherapy treatment with a cancer therapeutic vaccine, which comprises co-treatment of said patient along with a method as above disclosed. According to preferred embodiment, said cancer therapeutic vaccine is a viral based therapeutic vaccine. More preferably said viral based therapeutic vaccine is a MVA based therapeutic vaccine. Even more preferably, said MVA based therapeutic vaccine is carrying and expressing human papilloma virus 16 (HPV16) E6 and E7 oncoproteins and human interleukin-2 (e.g. TG4001 product) or is expressing the Muc1 antigen and the human interleukin-2 (e.g. TG4010 product).

The invention further includes post-treatment monitoring assays, following administration to a patient of an antibody able to bind to CSF-1R to assess efficacy of said treatment, and/or to evaluate the clinical outcome of the said treatment.

The monitoring assays include, but are not limited to, assays for circulating factors expressed and/or secreted by activated macrophages M1- or M2-polarized macrophages.

Factors expressed in the macrophage M2-type activation state include, but are not limited to IL-10, IL-6 and MCP-1. Factors expressed in the macrophage M1-type activation state may also be assayed, for example by measuring IL-12 levels, more particularly IL-12 P70 form levels. Driving macrophages towards a M1-type (macrophage M1 polarization-driven immune response and away from a M2-type (macrophage M2 polarization-driven immune response in patients can be appreciated by measuring increase of the IL12/IL10 ratio following administration to a patient of an antibody able to bind to CSF-1R of the Invention.

These tests can be derived from the patient's serum, blood, tissue, etc.

The invention further includes post-treatment monitoring assays, following administration to a patient of an antibody able to bind to CSF-1R to monitor macrophage activation and establish and/or maintain a proper dosage regimen.

In this case, it is possible to obtain a baseline levels by assaying for the presence of macrophages M1 and/or M2 in tissues, either directly or by means of factors expressed and/or secreted by activated macrophages and, then, following administration of an antibody able to bind to CSF-1R during treatment, monitor one or more times for the presence of M1 versus M2 macrophages in tissues (tumoral or normal tissues). One could then determine the optimized dose for treatment that will result in skewing from M2-type macrophages to M1-type macrophages response.

The invention provides materials and methods for assessing the efficacy of a treatment involving the administration of an antibody able to bind to CSF-1R to a patient using biological markers (biomarkers) that have been determined to be substantially reliable signature which correlates with the desired immune response. The biomarkers are present in biological samples obtained from the patient. The ability to predict the clinical outcome of a treatment, soon after its initiation, will enable clinicians and patients to identify ineffective therapy, make informed decisions regarding the course of treatment, including whether to abandon or to allow alternate therapy implementation.

The invention provides an ex-vivo method for assessing the efficacy of a treatment involving an antibody able to bind to CSF-1R to a patient.

According to the invention, the term "assessing" should be understood as "monitoring, modifying or adjusting" a treatment involving the administration of an antibody able to bind to CSF-1R to a patient.

In certain aspects the method includes assessing the efficacy of an antibody able to bind to CSF-1R based on the levels of interferon γ in the patient following immunotherapy treatment.

The monitoring assays include, but are not limited to, assays for circulating factors expressed and/or secreted by activated macrophages of M1 and/or M2 types.

Factors expressed in the macrophage M2-type activation state include, but are not limited to IL-6, MMP9 and MCP-1. Factors expressed in the macrophage M1-type activation state may also be assayed, for example by measuring IL-12 levels, more particularly IL-12 P70 form levels, or IL-12/IL-10 ratios.

In certain aspects, the method includes measuring a patient's levels of interleukin-6, interleukin-12, MMP9 and/or MCP-1 following administration into patient of an antibody able to bind to CSF-1R; and assessing the efficacy of the treatment based on the levels of the interleukin-6, interleukin-12, MMP9 and/or MCP-1.

In certain aspects, the method includes measuring a patient's levels of interleukin-6, interleukin-12, MMP9 and/or MCP-1 at least once several weeks following administration into patient of an antibody able to bind to CSF-1R; and assessing the efficacy of the immunotherapy treatment based on the levels of the interleukin-6, interleukin-12, MMP9 and/or MCP-1.

In certain aspects, the method can further include measuring a patient's levels of interleukin-6, interleukin-12, MMP9 and/or MCP-1 prior to administration of an antibody able to bind to CSF-1R. According to preferred embodiment, the values of patient's levels of interleukin-6, interleukin-12, MMP9 and/or MCP-1 measured before said administration of an antibody able to bind to CSF-1R are the "cut-off values" according to the present invention.

The time between the administration of an antibody able to bind to CSF-1R and interleukin-6, interleukin-12, MMP9 and/or MCP-1 measurements may be 1 day to about 48 weeks or more (e.g., from about 1 day to about 1 week, from about 1 week to about 2 weeks, from about 2 weeks to about 4 weeks, from about 4 weeks to about 8 weeks, from about 8 weeks to about 12 weeks, from about 12 weeks to about 16 weeks, from about 16 weeks to about 24 weeks, from about 24 weeks to about weeks, or more). In a preferred embodiment of the invention, the time interval is about 5 weeks. Similarly, additional measurements (i.e., a third, fourth, fifth, etc. measurement) may be taken at similar time intervals following the second measurement.

In related aspects the method includes determining the levels of interleukin-6, interleukin-12, MMP9 and/or MCP-1 in a patient following administration into patient of an antibody able to bind to CSF-1R; comparing said levels to a cut-off value; and assessing the efficacy of immunotherapy treatment based on the levels of interleukin-6, interleukin-12, MMP9 and/or MCP-1 compared to the "cut-off value".

According to special embodiment, the Invention concerns a method for assessing the efficacy of a treatment involving the administration of an antibody able to bind to CSF-1R to a patient comprising:
(i) administering one or more doses of said an antibody able to bind to CSF-1R to said subject;
(ii) measuring an interleukin-6, interleukin-12, MMP9 and/or MCP-1 level in the body of said subject following at least one of the said administration.

According to alternate embodiment of the invention, the method of the invention further comprises an initial step consisting in measuring the interleukin-6, interleukin-12, MMP9 and/or MCP-1 levels in the body of the patient before administration of the antibody able to bind to CSF-1R.

According to the present invention, the levels of interleukin-6, interleukin-12, MMP9 and/or MCP-1 are measured in a biological sample obtained from the patient. Biological samples include but are not limited to blood, serum, tissue, and other liquid samples of biological origin, solid tissue samples, such as a biopsy specimen. In a preferred embodiment, the biological sample is blood, plasma or serum, in which case obtaining the samples from a patient is relatively simple and non-invasive procedure. Methods of obtaining blood or serum are well-known in the art are not part of the invention.

In addition, numerous methods for detecting and quantifying polypeptides, including the instant biomarkers, are known. Such methods include but are not limited to antibody-based methods, more specifically monoclonal antibodies-based methods. The particular methods of detecting and quantifying the biomarkers are not important to the invention. For example the materials and methods of the present invention may be used with Luminex technology (Luminex Corporation, Austin, Tex.) or enzyme-linked immunosorbant assays (ELISA, numerous ELISA kits are commercially available e.g. by CliniScience, Diaclone, Biosource).

According to one embodiment of the Invention, the levels of interleukin-6, interleukin-12, MMP9 and/or MCP-1 are determined by using antibodies.

According to one specific embodiment of the Invention, said antibody(ies) is (are) specific of interleukin-6, interleukin-12, MMP9 or MCP-1.

According to one specific embodiment of the Invention, said antibodies are monoclonal antibodies.

According to one specific embodiment of the Invention, said antibodies are tagged for example by fluorescence, radio-label, enzyme, biotin, or any other methods designed to render cells labelled with said antibodies detectable. These techniques are widely used and known in the art.

The immunotherapy treatment of the Invention will be considered as efficient when the levels of interleukin-6, MMP9 and/or MCP-1 measured in patient following administration of an antibody able to bind to CSF-1R is below the levels of interleukin-6 and/or MCP-1, respectively, measured in patient before said administration (i.e. cut-off value).

Alternatively, the immunotherapy treatment of the Invention will be considered as efficient when the levels of interleukin-12 measured in patient following administration of an antibody able to bind to CSF-1R is above the levels of interleukin-12 measured in patient before said administration (i.e. cut-off value).

The invention further includes post-treatment monitoring assays, following administration to a patient of an antibody able to bind to CSF-1R to monitor macrophage activation and establish and/or maintain a proper dosage regimen.

In this case, it is possible to obtain a baseline levels by assaying for the presence of macrophages M1 and/or M2 in the circulation, either directly or by means of factors expressed and/or secreted by activated macrophages and, then, following administration of an antibody able to bind to CSF-1R during treatment, monitor one or more times for the presence of the macrophages in the circulation.

One could then determine the optimized dose for treatment that will result in skewing from an M2-type macrophage to an M1-type macrophage-driven response.

The methods of the invention are useful in treatment of disease involving inflammation and associated with CSF-1R.

FIGURE LEGENDS

FIG. 1: H27K15 is not cytotoxic to differentiating macrophages while other anti-CD115 mAbs induce massive cell death Cells were counted following a 6-day culture of monocytes with GM-CSF and CSF-1, in the presence or absence of anti-CD115 mAbs or F(ab')2 or with GW2580. Controls included cultures treated with rituximab or rituximab F(ab')2, or without any added compound. Shown are the means of cell counts in 5 microscope fields±standard deviation obtained in each culture condition.

Figure 2:
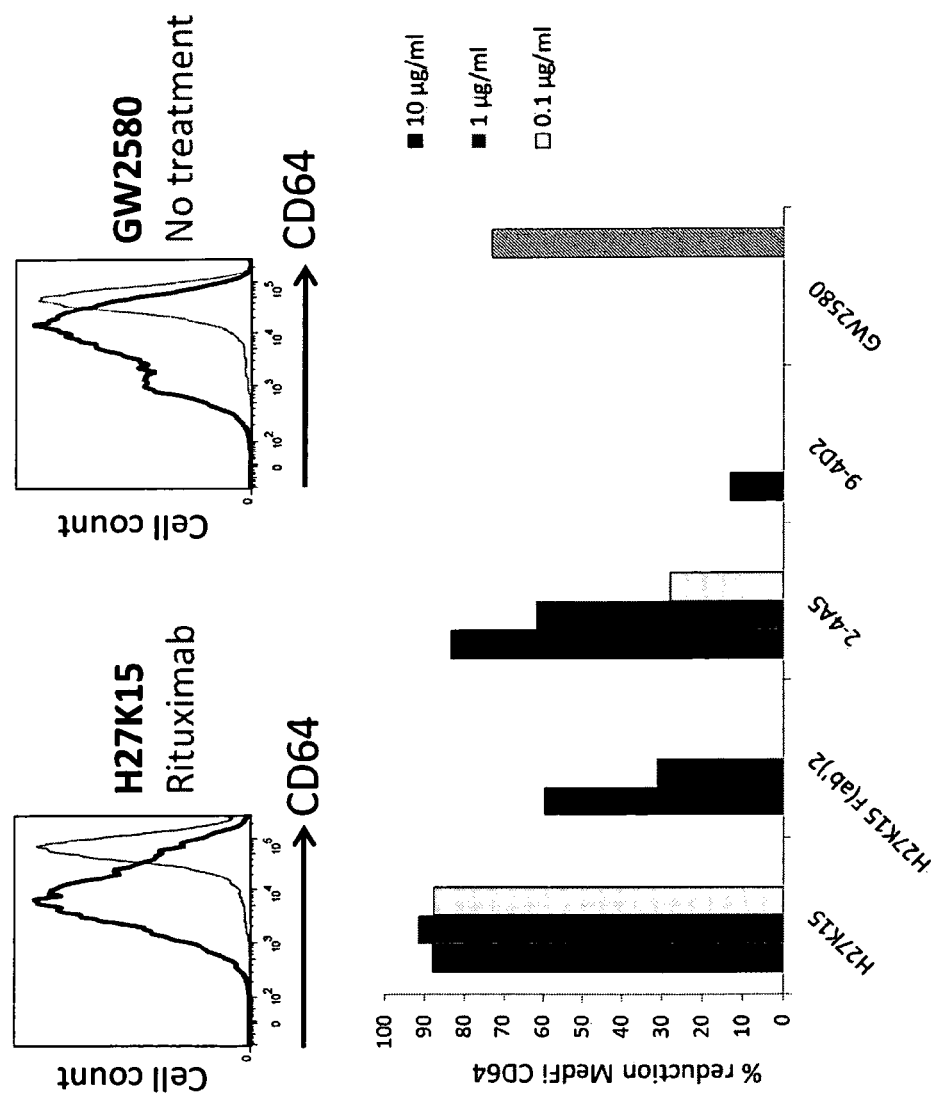

FIG. 2: Inhibition of CD64 (FcγRI) expression in human macrophages differentiated in the presence of monoclonal antibody H27K15

Macrophages obtained following a 6-day culture of monocytes from 3 different blood donors with GM-CSF and CSF-1 were analyzed by IC/FC for surface expression of CD64. Upper panels: CD64 staining in cultures from donor 1 treated with monoclonal antibody H27K15 (left, bold line) or with GW2580 (right, bold line) or their respective negative controls rituximab (left, thin line) or no treatment (right, thin line). Lower panel: Medians of fluorescence intensities in macrophage cultures treated with test compounds at 10, 1 or 0.1 μg/ml* were compared with those in the corresponding negative controls: H27K15 vs rituximab, H27K15-derived F(ab')$_2$ vs rituximab-derived F(ab')$_2$, mAbs 2-4A5 or 9-4D2 vs rat IgG1, GW2580 vs no treatment. Percentages of reduction in CD64 expression were calculated as: 100−[100×Median fluorescence intensity with test compound/Median fluorescence intensity with control]. Shown are the mean percentages of reduction in CD64 expression from the 3 blood donors. *except for the F(ab')$_2$ which were used at equimolar concentrations: 6.6; 0.6; and 0.06 μg/ml.

Figure 3:
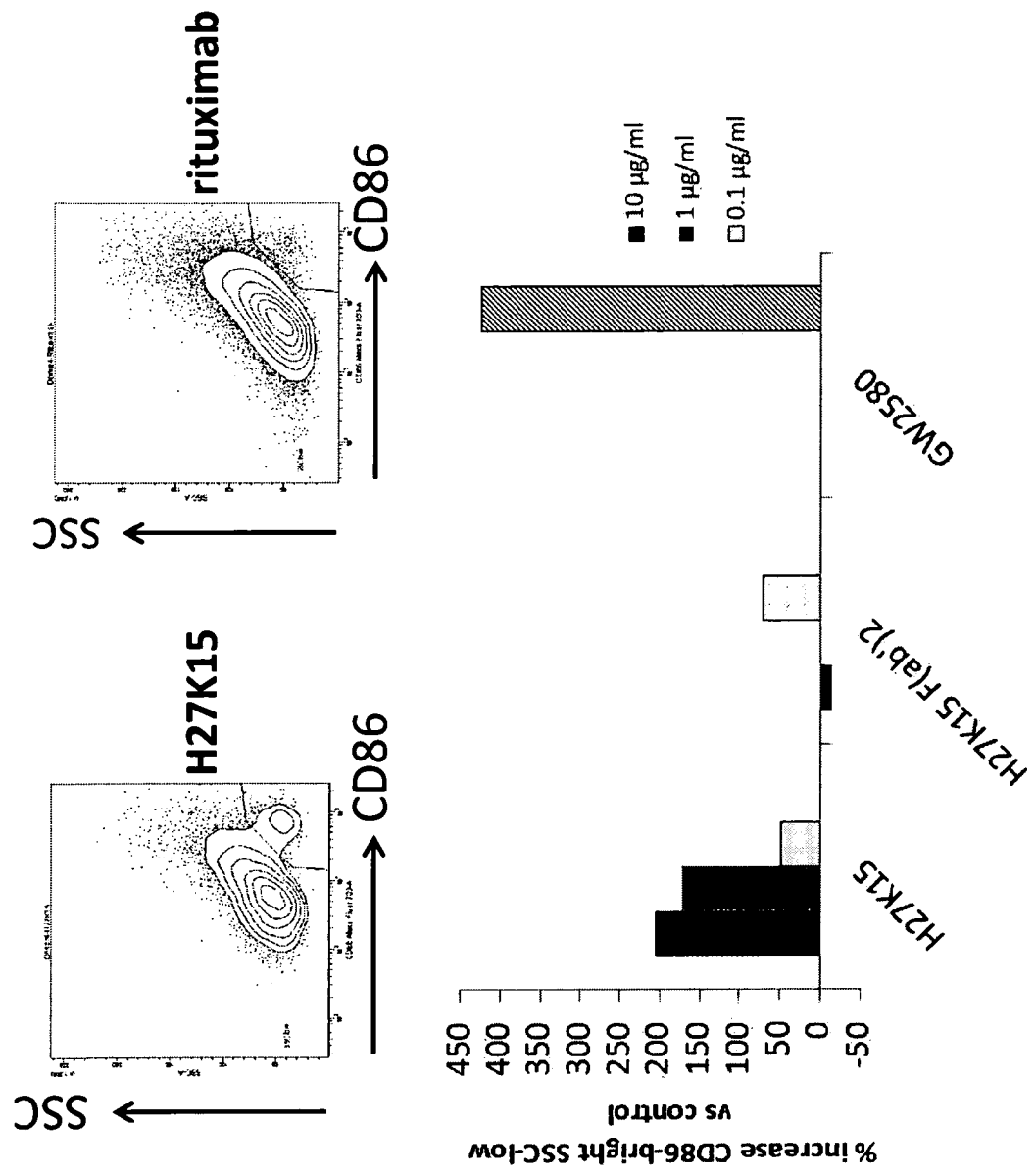

FIG. 3: Induction of a CD86$^{bright}$ SSC$^{low}$ macrophage population by H27K15

Upper panels: Dot plots showing CD86 staining (x-axis) and side scatter (SSC, y-axis) of macrophages from donor 3 differentiated for 6 days in the presence of H27K15 (left) or negative control rituximab (right). A gate was set on the CD86$^{bright}$ SSC$^{low}$ cell population induced by H27K15. Lower panel: Percentages of CD86$^{bright}$ SSC$^{low}$ cells with the test compounds at 10, 1 or 0.1 μg/ml* were compared with those in the corresponding negative controls: H27K15 vs rituximab, H27K15-derived F(ab')$_2$ vs rituximab-derived F(ab')$_2$, GW2580 vs no treatment. Percentages of increase in the CD86$^{bright}$ SSC$^{low}$ cell population were calculated as: 100×percentage of CD86$^{bright}$ SSC$^{low}$ cells with test compound/percentage of CD86$^{bright}$ SSC$^{low}$ cells with control. Shown are the mean percentages of increase in the CD86$^{bright}$ SSC$^{low}$ cell population from the 3 blood donors. *except for F(ab')$_2$: 6.6; 0.6; and 0.06 μg/ml.

Figure 4:
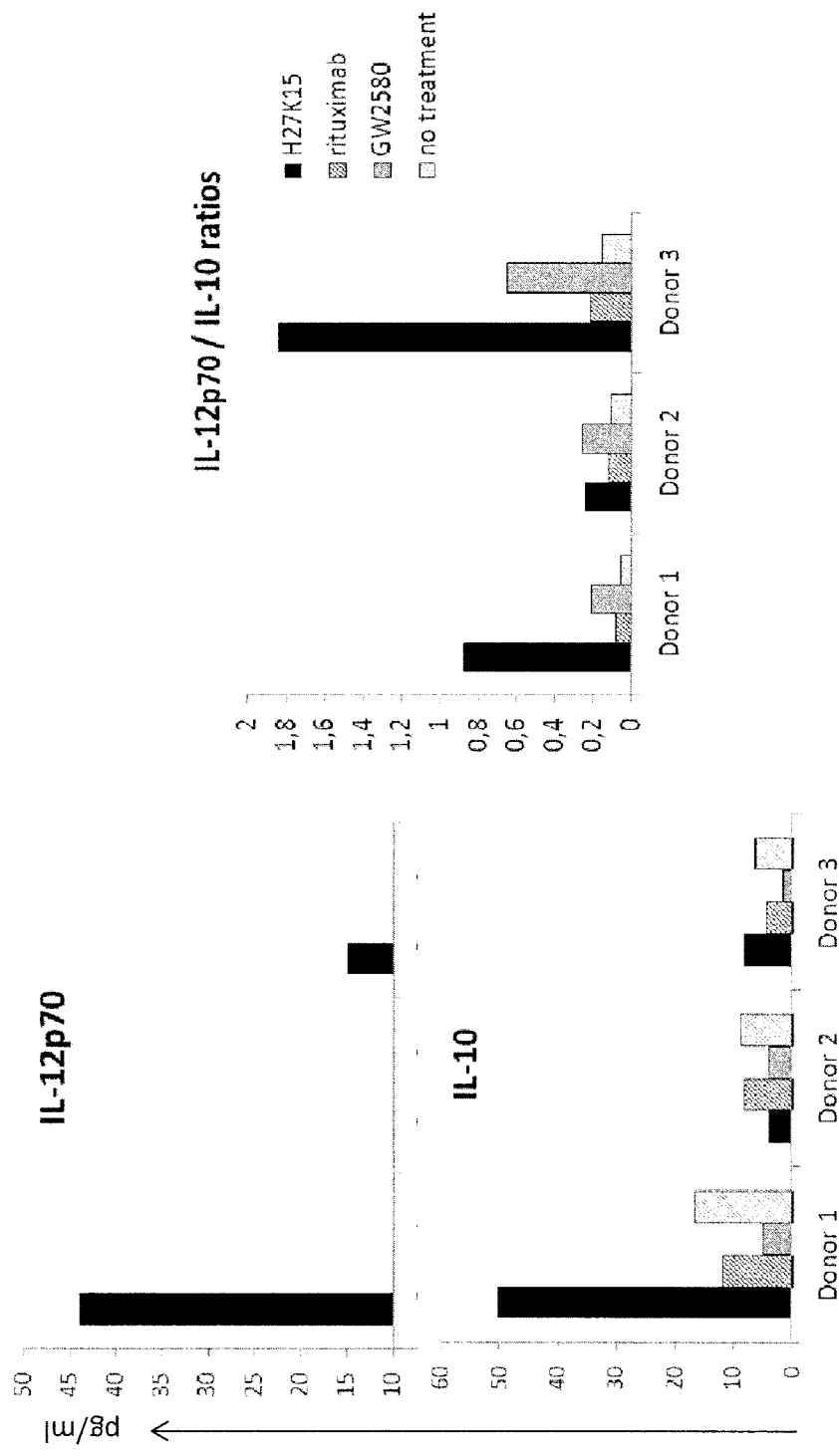

FIG. 4: H27K15 induces IL-12p70 secretion and increases macrophage IL-12/IL-10 ratios IL-12p70 and IL-10 were titrated in the culture supernatants from day-6 macrophages differentiated in the presence of mAb H27K15 (1 μg/ml), GW2580 (1 μM) or their respective negative controls rituximab or no treatment. Left panel: IL-12p70 and IL-10 levels (pg/ml) in macrophage cultures from 3 blood donors. Right: IL-12p70 (pg/ml)/IL-10 (pg/ml) ratios were calculated for each blood donor and each culture condition. In samples where IL-12p70 was undetectable (below the detection limit of 1 pg/m)l, its level was arbitrarily set at 1 pg/ml for the calculation of IL-12p70/IL-10 ratios.

Figure 5:
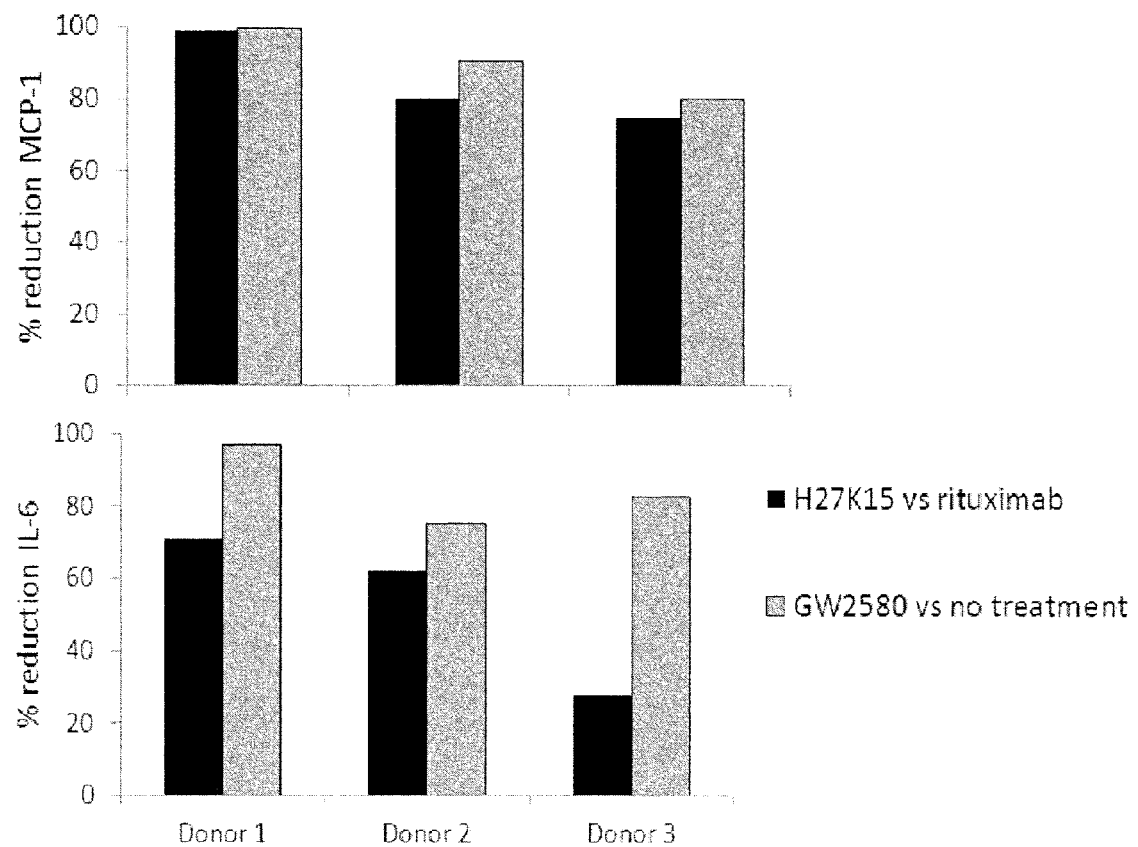

FIG. 5: H27K15 inhibits MCP-1/CCL2 and IL-6 secretion by macrophages

MCP-1 and IL-6 were titrated in the culture supernatants from day-6 macrophages differentiated in the presence of mAb H27K15 (1 μg/ml), GW2580 (1 μM) or their respective negative controls rituximab or no treatment. Percentages of reduction in MCP-1 (upper panel) or in IL-6 production (lower panel) were calculated for the 3 blood donors as: 100−[100×cytokine concentration with test compound (pg/ml)/cytokine concentration with control (pg/ml)].

Figure 6:
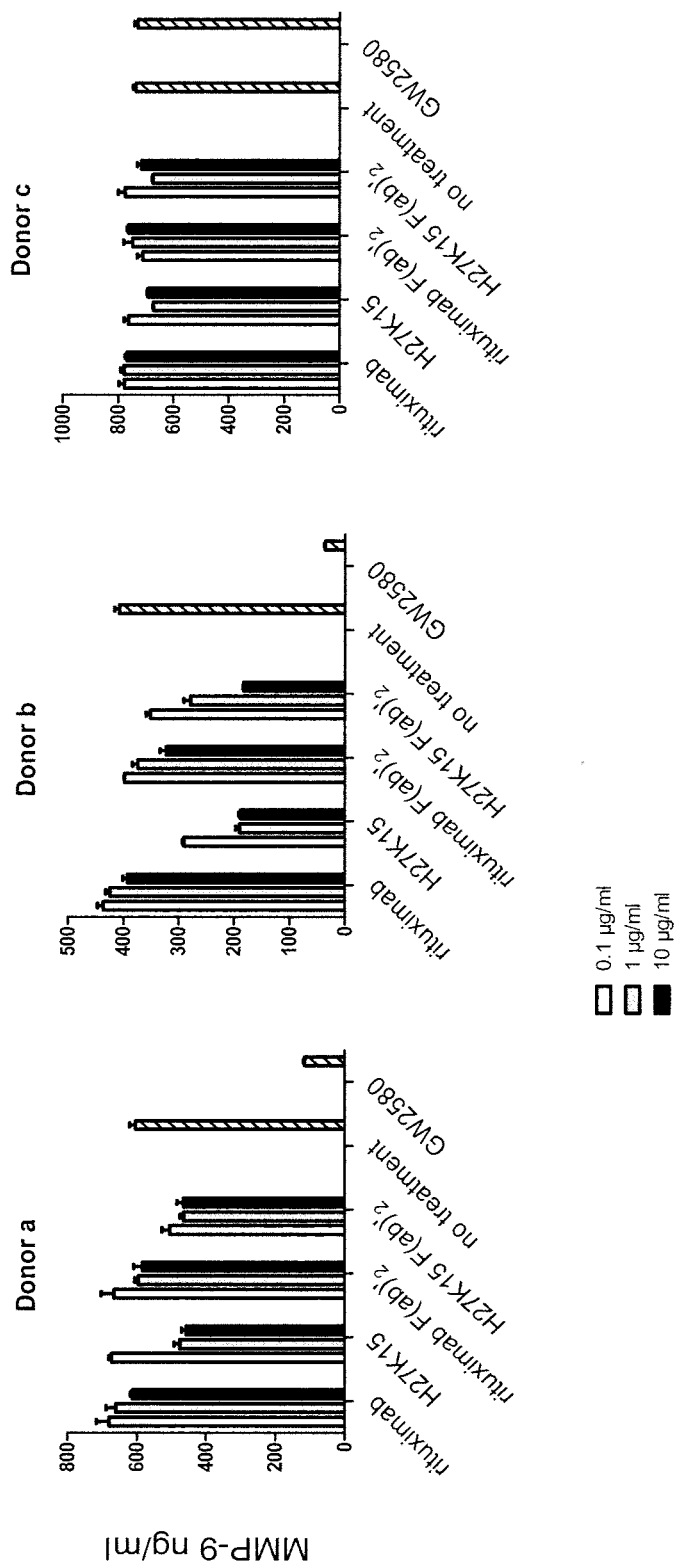

FIG. 6. Monocytes isolated from 3 different blood donors were differentiated for 6 days in the presence of GM-CSF and CSF-1, with or without mAb H27K15, Rituximab or GW2580. MAb H27K15 or Rituximab (0.1, 1 or 10 μg/ml) or equimolar concentrations of F(ab)'$_2$ derived from both mAbs were added to the cultures. MMP-9 was titrated by ELISA (R&D Systems) in day-6 culture supernatants.

Figure 7:
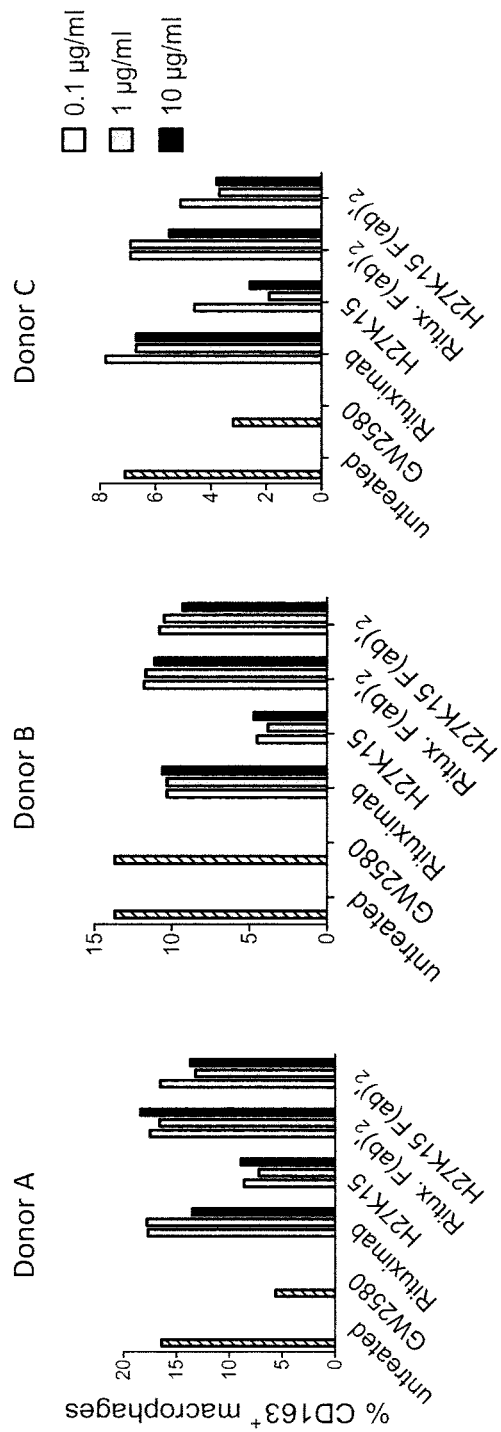

FIG. 7 Cells obtained after 6-day culture with GM-CSF and CSF-1 were harvested and incubated for 20 min at 4° C. with PBS containing human IgG Fc fragments to saturate Fc receptors. Fluorochrome-conjugated mAbs (anti-CD14-PerCP-Cy5.5, anti-CD163-PE, anti-CD206-APC, anti-CD1a-FITC, BD Biosciences) were then incubated with each sample for 20 min at 4° C. FCM analysis was performed using a FACS LSR-II (BD biosciences) with the DIVA software. Data from 3 different blood donors are presented.

Figure 8:
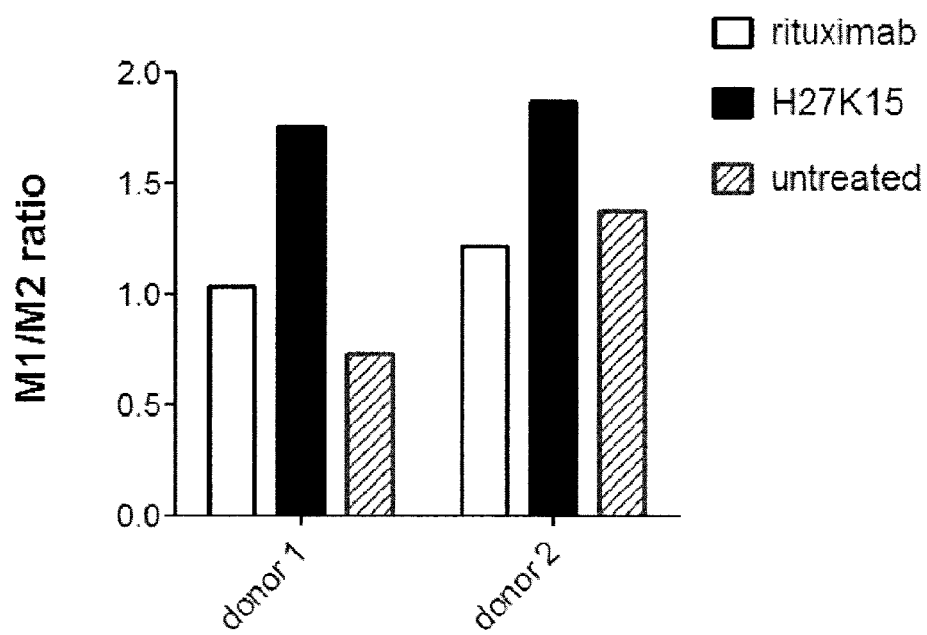

FIG. 8 Monocytes from 2 different donors were cultured with GM-CSF and CSF-1 in the presence or absence of anti-CD115 mAb H27K5 or control IgG1 rituximab at 1 μg/ml. Ratios between M1 (CD14$^+$CD163$^-$) and M2 (CD14$^4$CD163$^+$)-type macrophages among the macrophage population were determined after 6 days of cell differentiation.

EXAMPLES

The following commercial monoclonal antibodies were used throughout the study: anti-human CD115 mAb 2-4A5-4 (rat IgG$_{1,K}$, Santa Cruz), 9-4D2 (rat IgG1, Biolegend) and isotype control rat IgG1 (R&D Systems). mAb 1.2 SM is anti-CD115 mAb of sequence 1.2 SM published in patent application WO 2009/026303. Rituximab was obtained from Roche. F(ab')2 were produced at Transgene by pepsine digestion of the monoclonal antibodies, followed by purification by gel filtration.

Human Macrophage Differentiation Assay: Protocol

Buffy coats were provided by the Etablissement Francais du Sang (EFS, Strasbourg). Peripheral blood mononucleated cells (PBMC) were obtained by centrifugation on a ficoll gradient. Monocytes were purified by immunomagnetic cell sorting, using CD14-antibody-coated beads (Miltenyii). Enriched monocyte suspensions were more than 95% pure. Monocytes were differentiated for 6 days in 48-well plates (3×10$^5$ cells/well) in RPMI-Glutamax™ medium supplemented with 10% heat inactivated fetal calf serum and 1% tri-antibiotic mixture (penicillin, streptomycin, neomycin). GM-CSF (10 ng/ml) was added in the cell culture medium from day 0 to day 3. H27K15, other antibodies or internal control GW2580 (LC Labs) were added at day 0. On day 3 post-isolation, monocytes were washed with PBS and further cultivated in medium supplemented with CSF-1 (10 ng/ml) and GM-CSF (2 ng/ml), in the presence or absence of antibodies or GW2580. On day 6, supernatants were collected and stored at −20° C. Cells were detached from the plastic and pools of triplicates were analyzed by IC/FC (immunocytochemistry/flow cytometry) for cell sizes and expression of FcγR and CD86. Cytokines and chemokines were quantified in the culture supernatants by multiplex (Bioplex, Bio-Rad) or by ELISA.

For IC/FC analysis of macrophage cultures, pools of triplicates were centrifuged for 10 min at 1500 rpm and incubated for 20 min at 4° C. with PBS containing 10% human AB serum to saturate Fc receptors. Fluorochrome-conjugated mAbs anti-CD64-APC and anti-CD86-AI700, anti-CD64, -CD86, -CD163 and/or -CD14 (BD Biosciences) were then incubated with each sample for 20 min at 4° C. Cells were washed with PBS (5 min, 2000 rpm at 4° C.) and fixed with Cell-Fix (BD Biosciences, France). Flow cytometry analysis was performed using a FACS LSR-II (BD biosciences) with the DIVA software for acquisition and the Flow Jo software for analysis.

Results

Anti-CD115 mAb H27K15 is not cytotoxic to macrophages but polarizes their differentiation towards the M1 type To study whether mAb H27K15 could affect macrophage differentiation, purified CD14$^+$ monocytes were cultured for 7 days in the presence of GM-CSF and CSF-1, known to induce respectively M1- and M2-type macrophages (Akagawa K. S., 2002; Verreck F. A. et al., 2004). Three different doses of mab H27K15 or isotype control rituximab (0.1; 1 or 10 μg/ml) were added to the culture medium at the beginning of the culture and again 3 days later. F(ab')2 generated from H27K15 or from rituximab were tested in parallel at equivalent molar concentrations. F(ab')2 generated from mAb 1.2 SM (WO 2009/026303) was tested for comparison with the F(ab')2 derived from H27K15 or rituximab. The known blocking mAb to human CD115, 2-4A5, or the non-blocking mAb 9-4D2 (Sherr C. J. et al., 1989) were assayed and compared with isotype control rat IgG1. As another control, the small molecule CD115 tyrosine kinase inhibitor GW2580 was added to some of the cultures at 1 μM, a concentration previously shown to inhibit the CSF-1-dependent proliferation of human monocytes and the differentiation of murine macrophages in vitro (Conway J. G. et al., 2005; Paniagua R. T. et al., 2010).

Microscopical observation of day-6 cultures showed no obvious differences between wells treated with H27K15, Rituximab, mAb 9-4D2, IgG1, H27K15 F(ab')2 or Rituximab F(ab')2, compared with untreated cells, independently of the blood donor. For the wells treated with mAb SM1.2 F(ab')2, full cytotoxicity was observed for all donors for the 3 doses evaluated (0.066, 0.66 and 6.6 µg/ml). For the wells treated with mAb 2-4A5, full cytotoxicity was observed for all donors at the 2 highest doses tested (1 and 10 µg/ml). For the lowest dose (0.1 µg/ml), cytotoxicity was only partial. Altogether, those results did not reveal any toxicity of any antibody except for mAb SM1.2 F(ab')2 and mAb 2-4A5. For the cells with the control GW2580 at 1 µM, depending on the microscope field, a relative cytotoxicity was visualized as debris and less density of cells was observed in all blood donors. Cell viability was analyzed at day 6 by counting 5 microscope fields in each well of the plate (one in the center of the well and four fields at mid-distance between the center and the side of the well). Based on the above observations, numeration was done also for wells treated with compounds exhibiting partial or full cytotoxicity (mAb SM1.2 F(ab')2, mAb 2-4A5 and GW2580). FIG. 1 shows the means of 5 fields counted by individual well±standard deviation. Some antibodies exhibited partial or full cytotoxicity. Thus, the F(ab')2 derived from mAb SM1.2 had induced massive cell death at all concentrations and mAb 2-4A5 also dramatically reduced macrophage numbers, in comparison with their respective controls. In the presence of GW2580, approximately 70% of the macrophage number remained at day 6 compared with untreated cultures.

Day 6 cultures were analyzed by IC/FC for surface expression of the activating FcγR CD64 (FcγRI) and of the activation marker CD86. As shown on FIG. 2, surface expression of CD64 was drastically reduced upon treatment with H27K15 or with GW2580. H27K15 almost totally inhibited CD64 expression at all doses tested. Rat anti-human CD115 mAb 2-4A5 also decreased surface CD64 expression, but in a dose-dependent fashion. The non-CD115 blocking mAb 9-4D2 did not modify CD64 expression level. Interestingly, F(ab')$_2$ derived from H27K15 also down-regulated CD64 expression, but less potently than the full mAb and only when tested at 1 or 10 µg/ml, suggesting that the effect of H27K15 was partially Fc-dependent.

When the expression of the activation marker/co-stimulatory molecule CD86 was analyzed in day-6 macrophages, we found that a sub-population of cells characterized by the CD86$^{bright}$ SSC$^{low}$ phenotype had appeared in the cultures treated with either mAb H27K15 or with GW2580 (FIG. 3). Induction of this population of round-shaped cells expressing high levels of CD86 was not observed with H27K15-derived F(ab')$_2$, suggesting a role for H27K15 Fc region in this phenomenon. Gating on this population showed that CD86$^{bright}$ SSC$^{low}$ cells were mainly CD64$^{low}$ to CD64-negative (data not shown).

IL-12p70 and IL-10 were titrated in day-6 culture supernatants. Macrophages from the 3 donors tested did not produce any detectable IL-12p70 following culture with human IgG$_1$ rituximab or no reagent. Culture in the presence of mAb H27K15 induced IL-12p70 secretion by macrophages from 2 of the 3 blood donors. In contrast, IL-12p70 was not detectable after treatment with GW2580 (FIG. 4). IL-10, which was produced by resting macrophages from all donors, was up-regulated by H27K15 in macrophages from donor 1 but not in donor 2 and was only weakly increased in donor 3. As a result, IL-12p70/IL-ratios were up-regulated in the 3 blood donors tested (FIG. 4, right panel). Small molecule GW2580 also increased IL-12p70/IL-10 ratios, but rather due to the inhibition of IL-10 production.

These results show that targeting CD115 with mAb H27K15 on differentiating macrophages not only dramatically down-regulates the expression of CD64/FcγRI, but also induces a population of SSC$^{low}$ cells expressing high levels of the CD86 activation marker. In addition, H27K15 can induce IL-12p70 production and upregulates IL-12p70/IL-10 ratios in all donors, indicative of macrophage polarization towards M1-type.

Strikingly, production of the chemokine MCP-1/CCL2 was found to be almost totally suppressed when macrophages were differentiated in the presence of mAb H27K15 or GW2580 (FIG. 5, upper panel). Inhibition of MCP-1 secretion by H27K15 was effective in the 3 donors tested and ranged from 74% to 99%. Small molecule GW2580 was as efficacious as H27K15 in suppressing MCP-1 production. Levels of IL-6 in day-6 macrophage culture supernatants were also reduced by either H27K15 or GW2580 in all donors (FIG. 5, lower panel). Inhibition of IL-6 production was less drastic with H27K15 (from 27% to 70%) than with GW2580 (from 75 to 96%). H27K15-mediated inhibition of macrophage MCP-1 and IL-6 production (Roca H. et al., 2009), two soluble factors implicated in M2 macrophage polarization, is another piece of evidence indicating that the anti-CD115 mAb repolarizes macrophages towards M1.

Anti-CD115 mAb H27K15 Inhibits MMP-9 Production by Monocytes Cultured with GM-CSF and CSF-1

Tumor-associated macrophages are known to produce MMP-9 (matrix-metalloprotease 9), which promotes both tumor cell metastasis by degrading the extracellular matrix and neoangiogenesis by inducing VEGF release in the tumor microenvironment. MMP-9 produced by macrophages is a major regulator of the angiogenic switch in tumors.

CD14$^+$ monocytes from 3 different donors were allowed to differentiate in the presence of both GM-CSF and CSF-1, known to induce macrophage differentiation towards respectively the M1- and M2-types. MAb H27K15 or Rituximab (used as a negative control) were added to the cultures at 0.1, 1 or 10 µg/ml, Equimolar concentrations of F(ab)'$_2$ derived from both mAbs were assayed in parallel. The tyrosine kinase inhibitor GW2580, previously shown to inhibit the CSF-1-dependent proliferation of human monocytes and the differentiation of murine macrophages in vitro was tested in the same assay. After 6 days of culture, MMP-9 concentrations were measured in the supernatants by ELISA (FIG. 6). In 2 out of 3 donors tested, there was a dose-dependent decrease in MMP-9 production when cultures were treated with mAb H27K15 or with GW2580. With F(ab)'$_2$ derived from H27K15, there was an inhibitory effect in the same 2 donors. Thus, mAb H27K15 is capable of decreasing MMP-9 secretion by differentiating M2 macrophages.

These observations in macrophage cultures suggest that H27K15 administered to cancer patients may down-regulate MMP-9 concentration in the tumor microenvironment.

MAb H27K15 Inhibits the Differentiation of CD163-Positive M2-Type Macrophages

The hemoglobin scavenger receptor (CD163) has been identified as a marker of M2-polarized macrophages which is expressed by TAMs, notably in breast cancer. The surface expression of CD163 was analyzed by flow cytometry in day-6 macrophages derived from human monocytes cultured with GM-CSF and CSF-1. FIG. 7 shows the percentages of CD163-positive cells in differentiated cultures. Culture with mAb H27K15 inhibited the differentiation of the CD163$^+$ macrophage population in all 3 donors tested. In the presence of 1 μg/ml H27K15, percentages of CD163-positive cells decreased from 2.5 to 4 folds compared with control cultures treated with rituximab. GW2580 had the same effect in only ⅔ donors. F(ab)′₂ derived from H27K15 had weak or no effect on CD163 expression, indicating that the Fc region of the anti-CD115 mAb was involved in its mode of action.

As evidenced by these changes in surface CD163 expression and in agreement with the previous results, targeting CD115 with mAb H27K15 inhibits the differentiation of M2-type macrophages.

MAb H27K15 Skews Monocyte Differentiation from M2 to M1 Macrophages

The ratios between M1 and M2 macrophages were analyzed in cells derived from monocytes cultured with GM-CSF and CSF-1, in the presence or absence of mAb H27K15 or rituximab. After a 6-days culture of cells from 2 different blood donors, M1 (CD14⁺CD163⁻) versus M2 (CD14⁺CD163⁺) macrophages were quantified by flow cytometry. FIG. 8 shows the M1/M2 macrophage ratios calculated among the CD14⁺ macrophage population for each culture condition. MAb H27K15 at 1 μg/ml increased M1/M2 ratios in macrophages from the 2 donors tested, compared to control IgG1 rituximab at the same concentration or to untreated cultures.

Akagawa K. S. "Functional heterogeneity of colony-stimulating factor-induced human monocyte-derived macrophages." *International journal of hematology*. (2002) 76(1): 27-34.

Conway J. G., McDonald B., Parham J., Keith B., Rusnak D. W., Shaw E., Jansen M., Lin P., Payne A., Crosby R. M., Johnson J. H., Frick L., Lin M. H., Depee S., Tadepalli S., Votta B., James I., Fuller K., Chambers T. J., Kull F. C., Chamberlain S. D. and Hutchins J. T. "Inhibition of colony-stimulating-factor-1 signaling in vivo with the orally bioavailable cFMS kinase inhibitor GW2580." *Proceedings of the National Academy of Sciences of the United States of America*. (2005) 102(44): 16078-16083.

Paniagua R. T., Chang A., Mariano M. M., Stein E. A., Wang Q., Lindstrom T. M., Sharpe O., Roscow C., Ho P. P., Lee D. M. and Robinson W. H. "c-Fms-mediated differentiation and priming of monocyte lineage cells play a central role in autoimmune arthritis." *Arthritis research & therapy*. (2010) 12(1): R32.

Roca H., Varsos Z. S., Sud S., Craig M. J., Ying C. and Pienta K. J. "CCL2 and interleukin-6 promote survival of human CD11b+ peripheral blood mononuclear cells and induce M2-type macrophage polarization." *The Journal of biological chemistry*. (2009) 284(49): 34342-34354.

Sherr C. J., Ashmun R. A., Downing J. R., Ohtsuka M., Quan S. G., Golde D. W. and Roussel M. P. "Inhibition of colony-stimulating factor-1 activity by monoclonal antibodies to the human CSF-1 receptor." *Blood*. (1989) 73(7): 1786-1793.

Verreck F. A., de Boer T., Langenberg D. M., Hoeve M. A., Kramer M., Vaisberg H., Kastelein R., Kolk A., de Waal-Malefyt R. and Ottenhoff T. H. "Human IL-23-producing type 1 macrophages promote but IL-10-producing type 2 macrophages subvert immunity to (myco)bacteria." *Proceedings of the National Academy of Sciences of the United States of America*. (2004) 101(13): 4560-4565.

The invention claimed is:

1. A method for increasing a patient's pool of M1 macrophages, wherein the patient is suffering from one or more conditions associated with undesirable M2 macrophage activation, wherein said method comprises administering to the patient a monoclonal antibody, capable of binding to colony-stimulating factor-1 receptor (CSF-1R), in an amount effective to increase the patient's pool of M1 macrophages, wherein the antibody binds to an epitope comprising residues at or between amino acids 20 to 41 of SEQ ID NO:23.

2. The method of claim 1, wherein the patient is further suffering from one or more conditions associated with CSF-1R activity.

3. The method of claim 1, wherein the method decreases the patient's M2 macrophage pool.

4. The method of claim 1, wherein the method inhibits macrophage monocyte chemotactic protein 1 (MCP-1), interleukin 10 (IL10), and IL-6 production.

5. The method of claim 1, wherein the method down regulates surface FcγRI (CD64) and FcγRIII (CD16) expression on macrophages.

6. The method of claim 1, wherein the method promotes IL-12 production by macrophages.

7. The method of claim 1, wherein the method reduces at least one of the following:
   (i) tumor-associated macrophage (TAM) recruitment into tumor;
   (ii) at least one macrophage pro-tumoral function;
   (iii) tumor angiogenesis;
   (iv) tumor invasion and metastasis;
   (v) tumor growth; and
   (vi) tumor cell proliferation.

8. The method of claim 1, wherein the one or more conditions associated with undesirable M2 activation comprises cancer, asthma, allergy, or a progressive fibrosis disease.

9. The method of claim 1, wherein the antibody that is able to bind to CSF-1R binds to at least one epitope comprising residues located at or between amino acids 20 and 39 of SEQ ID NO:23.

10. The method of claim 1, wherein the antibody that is able to bind to CSF-1R does not compete with IL-34 for binding to CSF-1R.

11. The method of claim 1, wherein the antibody that is able to bind to CSF-1R competes with CSF-1 for binding to CSF-1R.

12. The method of claim 1, wherein the antibody that is able to bind to CSF-1R binds to human CSF-1R, wherein the antibody comprises:
   a heavy chain variable region comprising complementarity determining regions (CDR) CDR1, CDR2, and CDR3 comprising the sequences of SEQ ID NO:5, 6, and 7, respectively; and
   a light chain variable region comprising CDR1, CDR2, and CDR3 comprising the sequences of SEQ ID NO:8, 9, and 10, respectively.

13. The method of claim 1, wherein the antibody that is able to bind to CSF-1R comprises (a) a heavy chain amino acid sequence comprising SEQ ID NO:24, and (b) a light chain amino acid sequence comprising SEQ ID NO:28.

14. The method of claim 1, wherein the antibody that is able to bind to CSF-1R further binds to amino acids Asn72, Ser94-Ala95-Ala96, Lys102, Asp131-Pro132-Val133 and Trp159 of SEQ ID NO:23.

\* \* \* \* \*

UNITED STATES PATENT AND TRADEMARK OFFICE
CERTIFICATE OF CORRECTION

PATENT NO.        : 9,139,652 B2
APPLICATION NO.   : 14/352262
DATED             : September 22, 2015
INVENTOR(S)       : Haegel et al.

It is certified that error appears in the above-identified patent and that said Letters Patent is hereby corrected as shown below:

On the Title Page, Item (71), "Illkrich (FR)" should read --Illkirch (FR)--.

On the Title Page, Item (57), line 5, "CSF-IR" should read --CSF-1R--.

On the Title Page, Item (57), line 7, "CSF-IR" should read --CSF-1R--.

On the Title Page, Item (57), line 11, "CSF-IR" should read --CSF-1R--.

Signed and Sealed this
Fifth Day of April, 2016

Michelle K. Lee
*Director of the United States Patent and Trademark Office*

SEQUENCE LISTING

```
<160> NUMBER OF SEQ ID NOS: 33

<210> SEQ ID NO 1
<211> LENGTH: 467
<212> TYPE: PRT
<213> ORGANISM: Mus musculus

<400> SEQUENCE: 1

Met Tyr Leu Gly Leu Asn Tyr Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asp Trp Val Arg Gln Ser Pro Glu Met Gly Leu
    50                  55                  60

Glu Trp Val Ala Glu Ile Arg Ser Lys Ala Asn Asn His Ala Thr Phe
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Ser Leu Arg Pro Glu Asp Thr
            100                 105                 110

Gly Ile Tyr Tyr Cys Thr Arg Val Lys Val Gly Phe Asp Asn Trp Gly
        115                 120                 125

Gln Gly Thr Thr Leu Thr Val Ser Ser Ala Lys Thr Thr Ala Pro Ser
    130                 135                 140

Val Tyr Pro Leu Ala Pro Val Cys Gly Asp Thr Thr Gly Ser Ser Val
145                 150                 155                 160

Thr Leu Gly Cys Leu Val Lys Gly Tyr Phe Pro Glu Pro Val Thr Leu
```

```
            165                 170                 175
Thr Trp Asn Ser Gly Ser Leu Ser Ser Gly Val His Thr Phe Pro Ala
            180                 185                 190

Val Leu Gln Ser Asp Leu Tyr Thr Leu Ser Ser Val Thr Val Thr
            195                 200                 205

Ser Ser Thr Trp Pro Ser Gln Ser Ile Thr Cys Asn Val Ala His Pro
    210                 215                 220

Ala Ser Ser Thr Lys Val Asp Lys Lys Ile Glu Pro Arg Gly Pro Thr
225                 230                 235                 240

Ile Lys Pro Cys Pro Pro Cys Lys Cys Pro Ala Pro Asn Leu Leu Gly
                245                 250                 255

Gly Pro Ser Val Phe Ile Phe Pro Pro Lys Ile Lys Asp Val Leu Met
                260                 265                 270

Ile Ser Leu Ser Pro Ile Val Thr Cys Val Val Val Asp Val Ser Glu
            275                 280                 285

Asp Asp Pro Asp Val Gln Ile Ser Trp Phe Val Asn Asn Val Glu Val
    290                 295                 300

His Thr Ala Gln Thr Gln Thr His Arg Glu Asp Tyr Asn Ser Thr Leu
305                 310                 315                 320

Arg Val Val Ser Ala Leu Pro Ile Gln His Gln Asp Trp Met Ser Gly
                325                 330                 335

Lys Glu Phe Lys Cys Lys Val Asn Asn Lys Asp Leu Pro Ala Pro Ile
                340                 345                 350

Glu Arg Thr Ile Ser Lys Pro Lys Gly Ser Val Arg Ala Pro Gln Val
            355                 360                 365

Tyr Val Leu Pro Pro Pro Glu Glu Glu Met Thr Lys Lys Gln Val Thr
    370                 375                 380

Leu Thr Cys Met Val Thr Asp Phe Met Pro Glu Asp Ile Tyr Val Glu
385                 390                 395                 400

Trp Thr Asn Asn Gly Lys Thr Glu Leu Asn Tyr Lys Asn Thr Glu Pro
                405                 410                 415

Val Leu Asp Ser Asp Gly Ser Tyr Phe Met Tyr Ser Lys Leu Arg Val
            420                 425                 430

Glu Lys Lys Asn Trp Val Glu Arg Asn Ser Tyr Ser Cys Ser Val Val
    435                 440                 445

His Glu Gly Leu His Asn His His Thr Thr Lys Ser Phe Ser Arg Thr
450                 455                 460

Pro Gly Lys
465

<210> SEQ ID NO 2
<211> LENGTH: 234
<212> TYPE: PRT
<213> ORGANISM: Mus musculus

<400> SEQUENCE: 2

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ala Ser Leu Ser
            20                  25                  30

Val Ser Val Gly Glu Thr Val Thr Ile Thr Cys Arg Ala Ser Glu Asn
        35                  40                  45

Ile Tyr Ser Asn Leu Ala Trp Tyr Gln Gln Lys Gln Gly Lys Ser Pro
    50                  55                  60
```

```
Gln Leu Leu Val His Ala Ala Thr Asn Leu Ala Asp Gly Val Pro Ser
 65                  70                  75                  80

Arg Phe Ser Gly Ser Gly Ser Gly Thr Gln Tyr Ser Leu Lys Ile Asn
                 85                  90                  95

Ser Leu Gln Ser Glu Asp Phe Gly Ser Tyr Tyr Cys Gln His Phe Trp
            100                 105                 110

Gly Thr Pro Arg Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 3
<211> LENGTH: 118
<212> TYPE: PRT
<213> ORGANISM: Mus musculus

<400> SEQUENCE: 3

Glu Val Lys Leu Glu Glu Ser Gly Gly Gly Leu Val Gln Pro Gly Gly
 1               5                  10                  15

Ser Met Lys Leu Ser Cys Ala Ala Ser Gly Phe Thr Phe Ser Asp Ala
             20                  25                  30

Trp Met Asp Trp Val Arg Gln Ser Pro Glu Met Gly Leu Glu Trp Val
         35                  40                  45

Ala Glu Ile Arg Ser Lys Ala Asn Asn His Ala Thr Phe Tyr Ala Glu
 50                  55                  60

Ser Val Lys Gly Arg Phe Thr Ile Ser Arg Asp Asp Ser Lys Ser Ser
 65                  70                  75                  80

Val Tyr Leu Gln Met Asn Ser Leu Arg Pro Glu Asp Thr Gly Ile Tyr
             85                  90                  95

Tyr Cys Thr Arg Val Lys Val Gly Phe Asp Asn Trp Gly Gln Gly Thr
        100                 105                 110

Thr Leu Thr Val Ser Ser
        115

<210> SEQ ID NO 4
<211> LENGTH: 107
<212> TYPE: PRT
<213> ORGANISM: Mus musculus

<400> SEQUENCE: 4

Asp Ile Gln Met Thr Gln Ser Pro Ala Ser Leu Ser Val Ser Val Gly
 1               5                  10                  15

Glu Thr Val Thr Ile Thr Cys Arg Ala Ser Glu Asn Ile Tyr Ser Asn
             20                  25                  30
```

```
Leu Ala Trp Tyr Gln Gln Lys Gln Gly Lys Ser Pro Gln Leu Leu Val
             35                  40                  45

His Ala Ala Thr Asn Leu Ala Asp Gly Val Pro Ser Arg Phe Ser Gly
 50                  55                  60

Ser Gly Ser Gly Thr Gln Tyr Ser Leu Lys Ile Asn Ser Leu Gln Ser
 65                  70                  75                  80

Glu Asp Phe Gly Ser Tyr Tyr Cys Gln His Phe Trp Gly Thr Pro Arg
                 85                  90                  95

Thr Phe Gly Gly Gly Thr Lys Leu Glu Ile Lys
            100                 105
```

<210> SEQ ID NO 5
<211> LENGTH: 8
<212> TYPE: PRT
<213> ORGANISM: Mus musculus

<400> SEQUENCE: 5

```
Gly Phe Thr Phe Ser Asp Ala Trp
 1               5
```

<210> SEQ ID NO 6
<211> LENGTH: 10
<212> TYPE: PRT
<213> ORGANISM: Mus musculus

<400> SEQUENCE: 6

```
Ile Arg Ser Lys Ala Asn Asn His Ala Thr
 1               5                  10
```

<210> SEQ ID NO 7
<211> LENGTH: 9
<212> TYPE: PRT
<213> ORGANISM: Mus musculus

<400> SEQUENCE: 7

```
Thr Arg Val Lys Val Gly Phe Asp Asn
 1               5
```

<210> SEQ ID NO 8
<211> LENGTH: 6
<212> TYPE: PRT
<213> ORGANISM: Mus musculus

<400> SEQUENCE: 8

```
Glu Asn Ile Tyr Ser Asn
 1               5
```

<210> SEQ ID NO 9
<211> LENGTH: 3
<212> TYPE: PRT
<213> ORGANISM: Mus musculus

<400> SEQUENCE: 9

```
Ala Ala Thr
 1
```

<210> SEQ ID NO 10
<211> LENGTH: 9
<212> TYPE: PRT
<213> ORGANISM: Mus musculus

<400> SEQUENCE: 10

```
Gln His Phe Trp Gly Thr Pro Arg Thr
```

```
<210> SEQ ID NO 11
<211> LENGTH: 5
<212> TYPE: PRT
<213> ORGANISM: Mus musculus

<400> SEQUENCE: 11

Asp Ala Trp Met Asp
1               5

<210> SEQ ID NO 12
<211> LENGTH: 19
<212> TYPE: PRT
<213> ORGANISM: Mus musculus

<400> SEQUENCE: 12

Glu Ile Arg Ser Lys Ala Asn Asn His Ala Thr Phe Tyr Ala Glu Ser
1               5                   10                  15

Val Lys Gly

<210> SEQ ID NO 13
<211> LENGTH: 7
<212> TYPE: PRT
<213> ORGANISM: Mus musculus

<400> SEQUENCE: 13

Val Lys Val Gly Phe Asp Asn
1               5

<210> SEQ ID NO 14
<211> LENGTH: 11
<212> TYPE: PRT
<213> ORGANISM: Mus musculus

<400> SEQUENCE: 14

Arg Ala Ser Glu Asn Ile Tyr Ser Asn Leu Ala
1               5                   10

<210> SEQ ID NO 15
<211> LENGTH: 7
<212> TYPE: PRT
<213> ORGANISM: Mus musculus

<400> SEQUENCE: 15

Ala Ala Thr Asn Leu Ala Asp
1               5

<210> SEQ ID NO 16
<211> LENGTH: 9
<212> TYPE: PRT
<213> ORGANISM: Mus musculus

<400> SEQUENCE: 16

Gln His Phe Trp Gly Thr Pro Arg Thr
1               5

<210> SEQ ID NO 17
<211> LENGTH: 7
<212> TYPE: PRT
<213> ORGANISM: Mus musculus

<400> SEQUENCE: 17

Gly Phe Thr Phe Ser Asp Ala
```

```
<210> SEQ ID NO 18
<211> LENGTH: 8
<212> TYPE: PRT
<213> ORGANISM: Mus musculus

<400> SEQUENCE: 18

Arg Ser Lys Ala Asn Asn His Ala
1               5

<210> SEQ ID NO 19
<211> LENGTH: 7
<212> TYPE: PRT
<213> ORGANISM: Mus musculus

<400> SEQUENCE: 19

Val Lys Val Gly Phe Asp Asn
1               5

<210> SEQ ID NO 20
<211> LENGTH: 11
<212> TYPE: PRT
<213> ORGANISM: Mus musculus

<400> SEQUENCE: 20

Arg Ala Ser Glu Asn Ile Tyr Ser Asn Leu Ala
1               5                   10

<210> SEQ ID NO 21
<211> LENGTH: 7
<212> TYPE: PRT
<213> ORGANISM: Mus musculus

<400> SEQUENCE: 21

Ala Ala Thr Asn Leu Ala Asp
1               5

<210> SEQ ID NO 22
<211> LENGTH: 9
<212> TYPE: PRT
<213> ORGANISM: Mus musculus

<400> SEQUENCE: 22

Gln His Phe Trp Gly Thr Pro Arg Thr
1               5

<210> SEQ ID NO 23
<211> LENGTH: 972
<212> TYPE: PRT
<213> ORGANISM: Homo sapiens

<400> SEQUENCE: 23

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80
```

-continued

```
Thr Tyr Arg Cys Thr Glu Pro Gly Asp Pro Leu Gly Gly Ser Ala Ala
                85                  90                  95
Ile His Leu Tyr Val Lys Asp Pro Ala Arg Pro Trp Asn Val Leu Ala
            100                 105                 110
Gln Glu Val Val Phe Glu Asp Gln Asp Ala Leu Leu Pro Cys Leu
        115                 120                 125
Leu Thr Asp Pro Val Leu Glu Ala Gly Val Ser Leu Val Arg Val Arg
130                 135                 140
Gly Arg Pro Leu Met Arg His Thr Asn Tyr Ser Phe Ser Pro Trp His
145                 150                 155                 160
Gly Phe Thr Ile His Arg Ala Lys Phe Ile Gln Ser Gln Asp Tyr Gln
                165                 170                 175
Cys Ser Ala Leu Met Gly Gly Arg Lys Val Met Ser Ile Ser Ile Arg
            180                 185                 190
Leu Lys Val Gln Lys Val Ile Pro Gly Pro Ala Leu Thr Leu Val
        195                 200                 205
Pro Ala Glu Leu Val Arg Ile Arg Gly Glu Ala Ala Gln Ile Val Cys
    210                 215                 220
Ser Ala Ser Ser Val Asp Val Asn Phe Asp Val Phe Leu Gln His Asn
225                 230                 235                 240
Asn Thr Lys Leu Ala Ile Pro Gln Gln Ser Asp Phe His Asn Asn Arg
                245                 250                 255
Tyr Gln Lys Val Leu Thr Leu Asn Leu Asp Gln Val Asp Phe Gln His
            260                 265                 270
Ala Gly Asn Tyr Ser Cys Val Ala Ser Asn Val Gln Gly Lys His Ser
        275                 280                 285
Thr Ser Met Phe Phe Arg Val Val Glu Ser Ala Tyr Leu Asn Leu Ser
    290                 295                 300
Ser Glu Gln Asn Leu Ile Gln Glu Val Thr Val Gly Glu Gly Leu Asn
305                 310                 315                 320
Leu Lys Val Met Val Glu Ala Tyr Pro Gly Leu Gln Gly Phe Asn Trp
                325                 330                 335
Thr Tyr Leu Gly Pro Phe Ser Asp His Gln Pro Glu Pro Lys Leu Ala
            340                 345                 350
Asn Ala Thr Thr Lys Asp Thr Tyr Arg His Thr Phe Thr Leu Ser Leu
        355                 360                 365
Pro Arg Leu Lys Pro Ser Glu Ala Gly Arg Tyr Ser Phe Leu Ala Arg
    370                 375                 380
Asn Pro Gly Gly Trp Arg Ala Leu Thr Phe Glu Leu Thr Leu Arg Tyr
385                 390                 395                 400
Pro Pro Glu Val Ser Val Ile Trp Thr Phe Ile Asn Gly Ser Gly Thr
                405                 410                 415
Leu Leu Cys Ala Ala Ser Gly Tyr Pro Gln Pro Asn Val Thr Trp Leu
            420                 425                 430
Gln Cys Ser Gly His Thr Asp Arg Cys Asp Glu Ala Gln Val Leu Gln
        435                 440                 445
Val Trp Asp Asp Pro Tyr Pro Glu Val Leu Ser Gln Glu Pro Phe His
    450                 455                 460
Lys Val Thr Val Gln Ser Leu Leu Thr Val Glu Thr Leu Glu His Asn
465                 470                 475                 480
Gln Thr Tyr Glu Cys Arg Ala His Asn Ser Val Gly Ser Gly Ser Trp
                485                 490                 495
```

```
Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
        515                 520                 525

Leu Leu Leu Leu Leu Leu Leu Leu Tyr Lys Tyr Lys Gln Lys Pro
    530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
    610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
        675                 680                 685

Pro Gly Gln Asp Pro Glu Gly Gly Val Asp Tyr Lys Asn Ile His Leu
    690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Asn Asp Ser
                725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
        755                 760                 765

Leu Ala Ser Lys Asn Cys Ile His Arg Asp Val Ala Ala Arg Asn Val
    770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
        835                 840                 845

Phe Ser Leu Gly Leu Asn Pro Tyr Pro Gly Ile Leu Val Asn Ser Lys
    850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
```

```
                915                 920                 925
Ser Ser Arg Ser Gly Gly Ser Gly Ser Ser Ser Glu Leu Glu Glu
        930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970
```

<210> SEQ ID NO 24
<211> LENGTH: 467
<212> TYPE: PRT
<213> ORGANISM: Mus musculus
<220> FEATURE:
<221> NAME/KEY: VARIANT
<222> LOCATION: (20)..(137)
<223> OTHER INFORMATION: sequence "H27 variable region"

<400> SEQUENCE: 24

```
Met Tyr Leu Gly Leu Asn Tyr Val Phe Ile Val Phe Leu Leu Asn Gly
1               5                   10                  15

Val Gln Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asp Ala Trp Met Asp Trp Val Arg Gln Ala Pro Gly Lys Gly Leu
50                  55                  60

Glu Trp Val Ala Glu Ile Arg Ser Lys Ala Asn Asn His Ala Thr Phe
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Ser Leu Lys Thr Glu Asp Thr
            100                 105                 110

Gly Val Tyr Tyr Cys Thr Arg Val Lys Val Gly Phe Asp Asn Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300
```

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
        340                 345                 350

Glu Lys Thr Ile Ser Lys Ala Lys Gly Gln Pro Arg Glu Pro Gln Val
    355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
450                 455                 460

Pro Gly Lys
465

<210> SEQ ID NO 25
<211> LENGTH: 467
<212> TYPE: PRT
<213> ORGANISM: Mus musculus
<220> FEATURE:
<221> NAME/KEY: VARIANT
<222> LOCATION: (20)..(137)
<223> OTHER INFORMATION: Sequence "H19 variable region"

<400> SEQUENCE: 25

Met Tyr Leu Gly Leu Asn Tyr Val Phe Ile Val Phe Leu Leu Asn Gly
1               5                   10                  15

Val Gln Ser Glu Val Gln Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Ser Asp Ala Trp Met Asp Trp Val Arg Gln Ser Pro Glu Met Gly Leu
    50                  55                  60

Glu Trp Val Ala Glu Ile Arg Ser Lys Ala Asn Asn His Ala Thr Phe
65                  70                  75                  80

Tyr Ala Glu Ser Val Lys Gly Arg Phe Thr Ile Ser Arg Asp Asp Ser
            85                  90                  95

Lys Ser Ser Val Tyr Leu Gln Met Asn Ser Leu Arg Ala Glu Asp Thr
        100                 105                 110

Gly Ile Tyr Tyr Cys Thr Arg Val Lys Val Gly Phe Asp Asn Trp Gly
    115                 120                 125

Gln Gly Thr Thr Leu Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
            165                 170                 175

```
Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
        260                 265                 270

Ile Ser Arg Thr Pro Glu Val Thr Cys Val Val Val Asp Val Ser His
    275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
        340                 345                 350

Glu Lys Thr Ile Ser Lys Ala Lys Gly Gln Pro Arg Glu Pro Gln Val
    355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
    450                 455                 460

Pro Gly Lys
465

<210> SEQ ID NO 26
<211> LENGTH: 234
<212> TYPE: PRT
<213> ORGANISM: Mus musculus
<220> FEATURE:
<221> NAME/KEY: VARIANT
<222> LOCATION: (21)..(127)
<223> OTHER INFORMATION: Sequence "K5 variable region"

<400> SEQUENCE: 26

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Val Ser Val Gly Asp Arg Val Thr Ile Thr Cys Arg Ala Ser Glu Asn
        35                  40                  45

Ile Tyr Ser Asn Leu Ala Trp Tyr Gln Gln Lys Pro Gly Lys Ala Pro
```

```
                50                  55                  60
Lys Leu Leu Val His Ala Ala Thr Asn Leu Glu Ser Gly Val Pro Ser
 65                  70                  75                  80

Arg Phe Ser Gly Ser Gly Ser Gly Thr Asp Tyr Thr Leu Thr Ile Ser
                     85                  90                  95

Ser Leu Gln Pro Glu Asp Phe Gly Thr Tyr Tyr Cys Gln His Phe Trp
                    100                 105                 110

Gly Thr Pro Arg Thr Phe Gly Gln Gly Thr Lys Leu Glu Ile Lys Arg
                115                 120                 125

Thr Val Ala Ala Pro Ser Val Phe Ile Phe Pro Pro Ser Asp Glu Gln
            130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 27
<211> LENGTH: 234
<212> TYPE: PRT
<213> ORGANISM: Mus musculus
<220> FEATURE:
<221> NAME/KEY: VARIANT
<222> LOCATION: (21)..(127)
<223> OTHER INFORMATION: Sequence "K12 variable region"

<400> SEQUENCE: 27

Met Ser Val Pro Thr Gln Val Leu Gly Leu Leu Leu Leu Trp Leu Thr
  1               5                  10                  15

Asp Ala Arg Cys Asp Ile Gln Met Thr Gln Ser Pro Ser Ser Leu Ser
                 20                  25                  30

Ala Ser Val Gly Asp Arg Val Thr Ile Thr Cys Arg Ala Ser Glu Asn
             35                  40                  45

Ile Tyr Ser Asn Leu Ala Trp Tyr Gln Gln Lys Asp Gly Lys Ser Pro
 50                  55                  60

Gln Leu Leu Val His Ala Ala Thr Asn Leu Ala Asp Gly Val Pro Ser
 65                  70                  75                  80

Arg Phe Ser Gly Ser Gly Ser Gly Thr Gln Tyr Ser Leu Thr Ile Ser
                     85                  90                  95

Ser Leu Gln Pro Glu Asp Phe Gly Ser Tyr Tyr Cys Gln His Phe Trp
                    100                 105                 110

Gly Thr Pro Arg Thr Phe Gly Gly Gly Thr Lys Leu Glu Ile Lys Arg
                115                 120                 125

Thr Val Ala Ala Pro Ser Val Phe Ile Phe Pro Pro Ser Asp Glu Gln
            130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175
```

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 28
<211> LENGTH: 234
<212> TYPE: PRT
<213> ORGANISM: Mus musculus
<220> FEATURE:
<221> NAME/KEY: VARIANT
<222> LOCATION: (21)..(127)
<223> OTHER INFORMATION: Sequence "K15 variable region"

<400> SEQUENCE: 28

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Glu Asn
        35                  40                  45

Ile Tyr Ser Asn Leu Ala Trp Tyr Gln Gln Lys Pro Gly Lys Ala Pro
    50                  55                  60

Lys Leu Leu Leu His Ala Ala Thr Asn Leu Ala Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Gln His Phe Trp
            100                 105                 110

Gly Thr Pro Arg Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 29
<211> LENGTH: 118
<212> TYPE: PRT
<213> ORGANISM: Mus musculus
<220> FEATURE:
<221> NAME/KEY: VARIANT
<222> LOCATION: (1)..(118)
<223> OTHER INFORMATION: Sequence "VH27"

-continued

```
<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Arg Ser Lys Ala Asn Asn His Ala Thr Phe Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Lys Thr Glu Asp Thr Gly Val Tyr
                85                  90                  95

Tyr Cys Thr Arg Val Lys Val Gly Phe Asp Asn Trp Gly Gln Gly Thr
            100                 105                 110

Leu Val Thr Val Ser Ser
        115

<210> SEQ ID NO 30
<211> LENGTH: 118
<212> TYPE: PRT
<213> ORGANISM: Mus musculus
<220> FEATURE:
<221> NAME/KEY: VARIANT
<222> LOCATION: (1)..(118)
<223> OTHER INFORMATION: Sequence "VH19"

<400> SEQUENCE: 30

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asp Ala
            20                  25                  30

Trp Met Asp Trp Val Arg Gln Ser Pro Glu Met Gly Leu Glu Trp Val
        35                  40                  45

Ala Glu Ile Arg Ser Lys Ala Asn Asn His Ala Thr Phe Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Thr Arg Val Lys Val Gly Phe Asp Asn Trp Gly Gln Gly Thr
            100                 105                 110

Thr Leu Thr Val Ser Ser
        115

<210> SEQ ID NO 31
<211> LENGTH: 107
<212> TYPE: PRT
<213> ORGANISM: Mus musculus
<220> FEATURE:
<221> NAME/KEY: VARIANT
<222> LOCATION: (1)..(107)
<223> OTHER INFORMATION: Sequence "VK5"

<400> SEQUENCE: 31

Asp Ile Gln Met Thr Gln Ser Pro Ser Ser Leu Ser Val Ser Val Gly
1               5                   10                  15

Asp Arg Val Thr Ile Thr Cys Arg Ala Ser Glu Asn Ile Tyr Ser Asn
```

```
                    20                  25                  30

Leu Ala Trp Tyr Gln Gln Lys Pro Gly Lys Ala Pro Lys Leu Leu Val
            35                  40                  45

His Ala Ala Thr Asn Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Gly Thr Tyr Tyr Cys Gln His Phe Trp Gly Thr Pro Arg
                85                  90                  95

Thr Phe Gly Gln Gly Thr Lys Leu Glu Ile Lys
                100                 105

<210> SEQ ID NO 32
<211> LENGTH: 107
<212> TYPE: PRT
<213> ORGANISM: Mus musculus
<220> FEATURE:
<221> NAME/KEY: VARIANT
<222> LOCATION: (1)..(107)
<223> OTHER INFORMATION: Sequence "VK12"

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
                20                  25                  30

Leu Ala Trp Tyr Gln Gln Lys Asp Gly Lys Ser Pro Gln Leu Leu Val
            35                  40                  45

His Ala Ala Thr Asn Leu Ala Asp Gly Val Pro Ser Arg Phe Ser Gly
    50                  55                  60

Ser Gly Ser Gly Thr Gln Tyr Ser Leu Thr Ile Ser Ser Leu Gln Pro
65                  70                  75                  80

Glu Asp Phe Gly Ser Tyr Tyr Cys Gln His Phe Trp Gly Thr Pro Arg
                85                  90                  95

Thr Phe Gly Gly Gly Thr Lys Leu Glu Ile Lys
                100                 105

<210> SEQ ID NO 33
<211> LENGTH: 107
<212> TYPE: PRT
<213> ORGANISM: Mus musculus
<220> FEATURE:
<221> NAME/KEY: VARIANT
<222> LOCATION: (1)..(107)
<223> OTHER INFORMATION: Sequence "VK15"

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
                20                  25                  30

Leu Ala Trp Tyr Gln Gln Lys Pro Gly Lys Ala Pro Lys Leu Leu Leu
            35                  40                  45

His Ala Ala Thr Asn Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Gly Thr Pro Arg
                85                  90                  95
```

```
Thr Phe Gly Gln Gly Thr Lys Leu Glu Ile Lys
            100                 105
```